United States Patent [19]
Schmidt et al.

[11] Patent Number: 5,925,645
[45] Date of Patent: Jul. 20, 1999

[54] 2-ARYL-SUBSTITUTED PYRIDINES

[75] Inventors: Gunter Schmidt, Wuppertal, Germany; Rolf Angerbauer, Kobe, Japan; Arndt Brandes; Michael Lögers, both of Wuppertal, Germany; Matthias Müller-Gliemann, Solingen, Germany; Hilmar Bischoff; Delf Schmidt, both of Wuppertal, Germany; Stefan Wohlfeil, Hilden, Germany

[73] Assignee: Bayer Aktiengesellschaft, Leverkusen, Germany

[21] Appl. No.: 08/816,290

[22] Filed: Mar. 13, 1997

[30] Foreign Application Priority Data

Mar. 20, 1996 [DE] Germany .............. 196 10 932

[51] Int. Cl.⁶ .............. A61K 31/44; C07D 213/30; C07D 213/50; C07D 213/38
[52] U.S. Cl. .............. 514/277; 514/357; 546/329; 546/333; 546/334; 546/339; 546/340; 546/343; 546/344; 546/346; 546/348; 546/350
[58] Field of Search .............. 514/277, 357; 546/329, 333, 334, 339, 340, 343, 344, 346, 348, 350

[56] References Cited

U.S. PATENT DOCUMENTS

| | | |
|---|---|---|
| 4,814,346 | 3/1989 | Albert et al. . |
| 4,925,852 | 5/1990 | Kesseler et al. . |
| 5,006,530 | 4/1991 | Angerbauer et al. . |
| 5,169,857 | 12/1992 | Angerbauer et al. . |
| 5,401,746 | 3/1995 | Angerbauer et al. . |
| 5,409,910 | 4/1995 | Angerbauer et al. . |

FOREIGN PATENT DOCUMENTS

| | | |
|---|---|---|
| 306929 | 3/1989 | European Pat. Off. . |
| 356788 | 3/1990 | European Pat. Off. . |

*Primary Examiner*—Patricia L. Morris
*Attorney, Agent, or Firm*—Sprung Kramer Schaefer & Briscoe

[57] ABSTRACT

The 2-aryl-substituted pyridines are prepared by reacting pyridylaldehydes with organometallic compounds and then selectively reducing the products. The 2-aryl-substituted pyridines are suitable as active compounds in medicaments, in particular in medicaments for the treatment of arteriosclerosis.

6 Claims, No Drawings

2-ARYL-SUBSTITUTED PYRIDINES

The present invention relates to 2-aryl-substituted pyridines, to processes for their preparation and to their use in medicaments.

U.S. Pat. No. 5,169,857 discloses 7-(polysubstituted pyridyl)-6-heptenoates for the treatment of arteriosclerosis, lipoproteinaemia and hyperproteinaemia. The preparation of 7-(4-aryl-3-pyridyl)-3,5-dihydroxy-6-heptenoates is additionally described in EP 325 130.

The present invention relates to 2-aryl-substituted pyridines of the general formula (I)

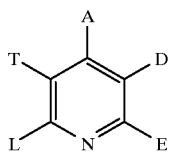

(I)

in which
  A and E are identical or different and represent aryl having 6 to 10 carbon atoms, which is optionally substituted up to 3 times identically or differently by halogen, hydroxyl, trifluoromethyl, trifluoromethoxy or by straight-chain or branched alkyl, acyl, hydroxyalkyl or alkoxy each having up to 7 carbon atoms, or by a group of the formula $-NR^1R^2$,
in which
  $R^1$ and $R^2$ are identical or different and denote hydrogen, phenyl or straight-chain or branched alkyl having up to 6 carbon atoms,
  D represents straight-chain or branched alkyl having up to 8 carbon atoms, which is substituted by hydroxyl,
  L represents cycloalkyl having 3 to 8 carbon atoms or straight-chain or branched alkyl having up to 8 carbon atoms, which is optionally substituted by cycloalkyl having 3 to 8 carbon atoms or by hydroxyl,
  T represents a radical of the formula

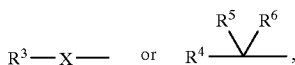

in which
  $R^3$ and $R^4$ are identical or different and denote cycloalkyl having 3 to 8 carbon atoms, or
    denote aryl having 6 to 10 carbon atoms, or a 5- to 7-membered aromatic, optionally benzo-fused heterocycle having up to 3 heteroatoms from the series S, N and/or O, each of which is optionally substituted up to 3 times identically or differently by trifluoromethyl, trifluoromethoxy, nitro, halogen, hydroxyl, carboxyl, by straight-chain or branched alkyl, acyl, alkoxy or alkoxycarbonyl each having up to 6 carbon atoms or by phenyl, phenoxy or phenylthio, which for their part can be substituted by halogen, trifluoromethyl or trifluoromethoxy,
    and/or the cycles are optionally substituted by a group of the formula $-NR^7R^8$,
in which
  $R^7$ and $R^8$ are identical or different and have the meaning of $R^1$ and $R^2$ indicated above,
  X denotes straight-chain or branched alkyl or alkenyl each having 2 to 10 carbon atoms, each of which is optionally substituted up to 2 times by hydroxyl or halogen,
  $R^5$ denotes hydrogen and
  $R^6$ denotes hydrogen, halogen, azido, trifluoromethyl, mercapto, hydroxyl, trifluoromethoxy, straight-chain or branched alkoxy having up to 5 carbon atoms or a radical of the formula $-NR^9R^{10}$,
in which
  $R^9$ and $R^{10}$ are identical or different and have the meaning of $R^1$ and $R^2$ indicated above,
or
  $R^5$ and $R^6$ together with the carbon atom form a carbonyl group,
and their salts.

The 2-aryl-substituted pyridines according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention, which have a free carboxyl group. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Heterocycle, optionally benzo-fused, in the context of the invention in general represents a saturated or unsaturated 5- to 7-membered, preferably 5- to 6-membered heterocycle, which can contain up to 3 heteroatoms from the series S, N and/or O. Examples which may be mentioned are: indolyl, isoquinolyl, quinolyl, benzo[b]thiophene, benzothiazolyl, benzo[b]furanyl, pyridyl, thienyl, furyl, pyrrolyl, thiazolyl, oxazolyl, imidazolyl, morpholinyl or piperidyl. Quinolyl, indolyl, pyridyl and benzothiazolyl are preferred.

Preferred compounds of the general formula (I) are those in which
  A and E are identical or different and represent phenyl or naphthyl, each of which is optionally substituted up to 2 times identically or differently by fluorine, chlorine, bromine, hydroxyl, trifluoromethyl, trifluoromethoxy, nitro or by straight-chain or branched alkyl, acyl or alkoxy each having up to 6 carbon atoms or by a group of the formula $-NR^1R^2$,
in which
  $R^1$ and $R^2$ are identical or different and denote hydrogen, phenyl or straight-chain or branched alkyl having up to 4 carbon atoms, D represents straight-chain or branched alkyl having up to 7 carbon atoms, which is substituted by hydroxyl, L represents cyclopropyl, cyclobutyl, cyclopentyl, cyclohexyl or cycloheptyl, or represents straight-chain or branched alkyl having up to 6 carbon atoms, which is optionally substituted by cyclopropyl, cyclobutyl, cyclopentyl, cyclohexyl, cycloheptyl or by hydroxyl, T represents a radical of the formula

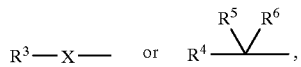

worin, in which $R^3$ and $R^4$ are identical or different and denote cyclopropyl, cyclopentyl or cyclohexyl, or denote naphthyl, phenyl, pyridyl, quinolyl, indolyl, benzothiazolyl or tetrahydronaphthalenyl, each of which is optionally substituted up to 3 times identically or differently by trifluoromethyl, trifluoromethoxy, fluorine, chlorine, bromine, hydroxyl, carboxyl, by straight-chain or branched alkyl, acyl, alkoxy or alkoxycarbonyl each having up to 5 carbon atoms or by phenyl, phenoxy or phenylthio, which for their part can be substituted by fluorine, chlorine, bromine, trifluoromethyl or trifluoromethoxy, and/or the cycles are optionally substituted by a group of the formula $-NR^7R^8$, in which $R^7$ and $R^8$ are identical or different and have the meaning of $R^1$ and $R^2$ indicated above, X is straight-chain or branched alkyl or alkenyl each having 2 to 8 carbon atoms, each of which is optionally substituted up to 2 times by hydroxyl or fluorine, $R^5$ denotes hydrogen and $R^6$ denotes hydrogen, fluorine, chlorine, bromine, azido, trifluoromethyl, hydroxyl, mercapto, trifluoromethoxy, straight-chain or branched alkoxy having up to 4 carbon atoms or a radical of the formula $-NR^9R^{10}$, in which $R^9$ and $R^{10}$ are identical or different and have the meaning of $R^1$ and $R^2$ indicated above, or $R^5$ and $R^6$ together with the carbon atom form a carbonyl group, and their salts.

Particularly preferred compounds of the general formula (I) are those in which

A and E are identical or different and represent phenyl or naphthyl, each of which is optionally substituted up to 2 times identically or differently by fluorine, chlorine, bromine, hydroxyl, trifluoromethyl, trifluoromethoxy, nitro or by straight-chain or branched alkyl or alkoxy each having up to 5 carbon atoms, D represents straight-chain or branched alkyl having up to 6 carbon atoms, which is substituted by hydroxyl, L represents cyclopropyl, cyclobutyl, cyclopentyl, cyclohexyl or cycloheptyl, or represents straight-chain or branched alkyl having up to 5 carbon atoms, which is optionally substituted by cyclopentyl or cyclohexyl, T represents a radical of the formula

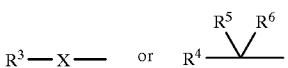

in which $R^3$ and $R^4$ are identical or different and denote cyclopropyl, phenyl, pyridyl, quinolyl, indolyl, naphthyl, benzothiazolyl or tetrahydronaphthalenyl, each of which is optionally substituted up to 2 times identically or differently by trifluoromethyl, trifluoromethoxy, fluorine, chlorine, bromine, hydroxyl, carboxyl, amino, by straight-chain or branched alkyl, alkoxy or alkoxycarbonyl each having up to 4 carbon atoms or by phenyl, phenoxy or phenylthio, which for their part can be substituted by fluorine, chlorine, bromine, trifluoromethyl or trifluoromethoxy, X denotes straight-chain or branched alkyl or alkenyl having 2 to 6 carbon atoms, each of which is optionally substituted up to 2 times by hydroxyl or fluorine, $R^5$ denotes hydrogen and $R^6$ denotes hydrogen, fluorine, chlorine, bromine, azido, trifluoromethyl, amino, hydroxyl, trifluoromethoxy, methoxy or mercapto, or $R^5$ and $R^6$ together with the carbon atom form a carbonyl group, and their salts.

Very particularly preferred compounds of the general formula (I) according to the invention are those in which A represents phenyl, which is optionally substituted up to 2 times identically or differently by fluorine, chlorine, methyl, nitro or methoxy.

A process for the preparation of the compounds of the general formula (I) according to the invention has additionally been found, characterized in that compounds of the general formula (II) or (III)

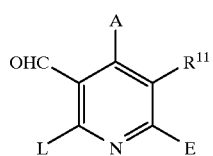

(II)

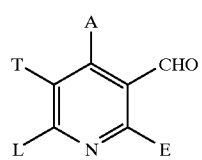

(III)

in which

A, E, L and T have the meaning indicated above and $R^{11}$ represents straight-chain or branched alkoxycarbonyl having up to 4 carbon atoms, are either reacted first with organometallic reagents, in particular Grignard or Wittig reagents, in inert solvents, further derivatization is optionally carried out according to customary methods and the products are then reduced in inert solvents, or in the case of the compounds of the general formula (III) direct reductions, optionally by means of several stages, are carried out.

The processes according to the invention can be illustrated by way of example by the following reaction scheme:
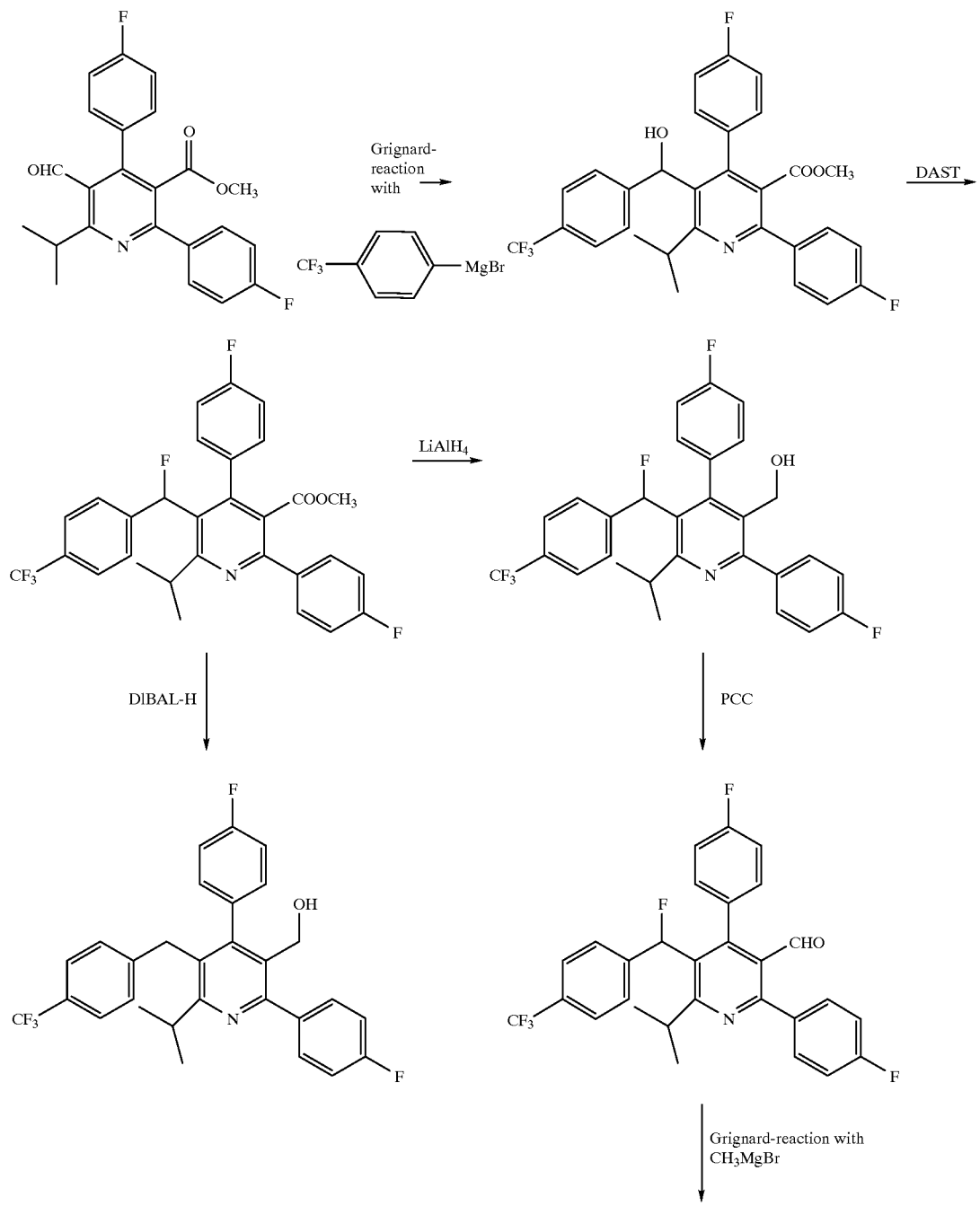

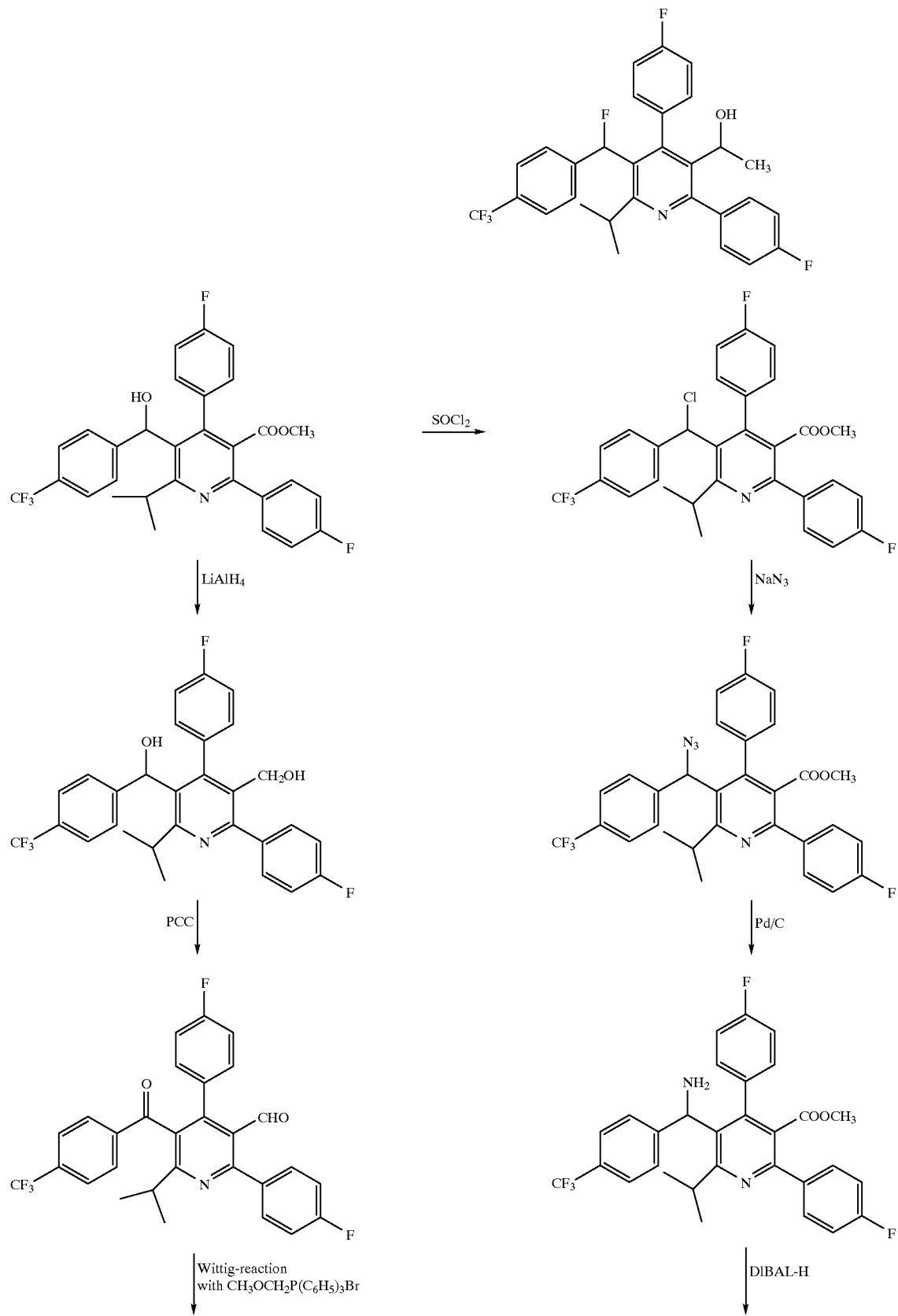

9
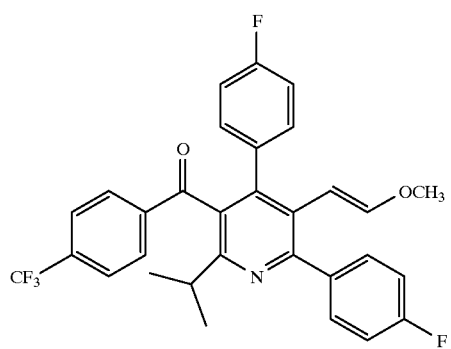
1) NaI/TMS-Chloride
2) NaBH₄ ↓
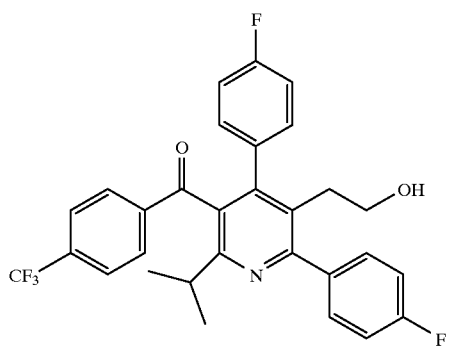
10
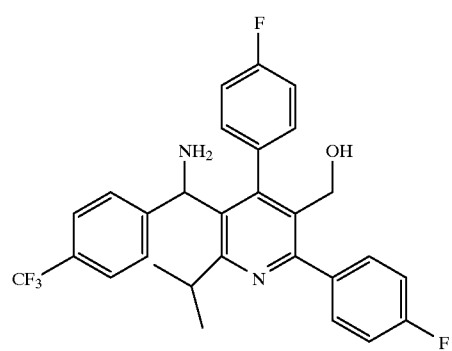
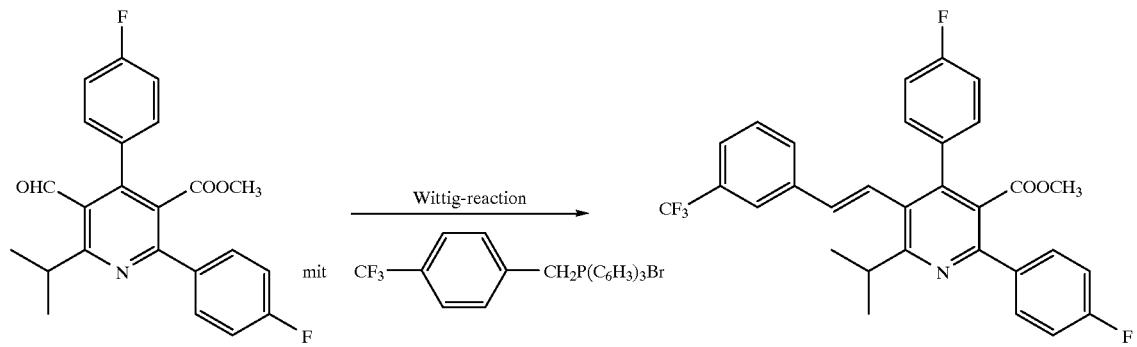
DIBAL-H ↙   Hydroxylation/OsO₄ ↓

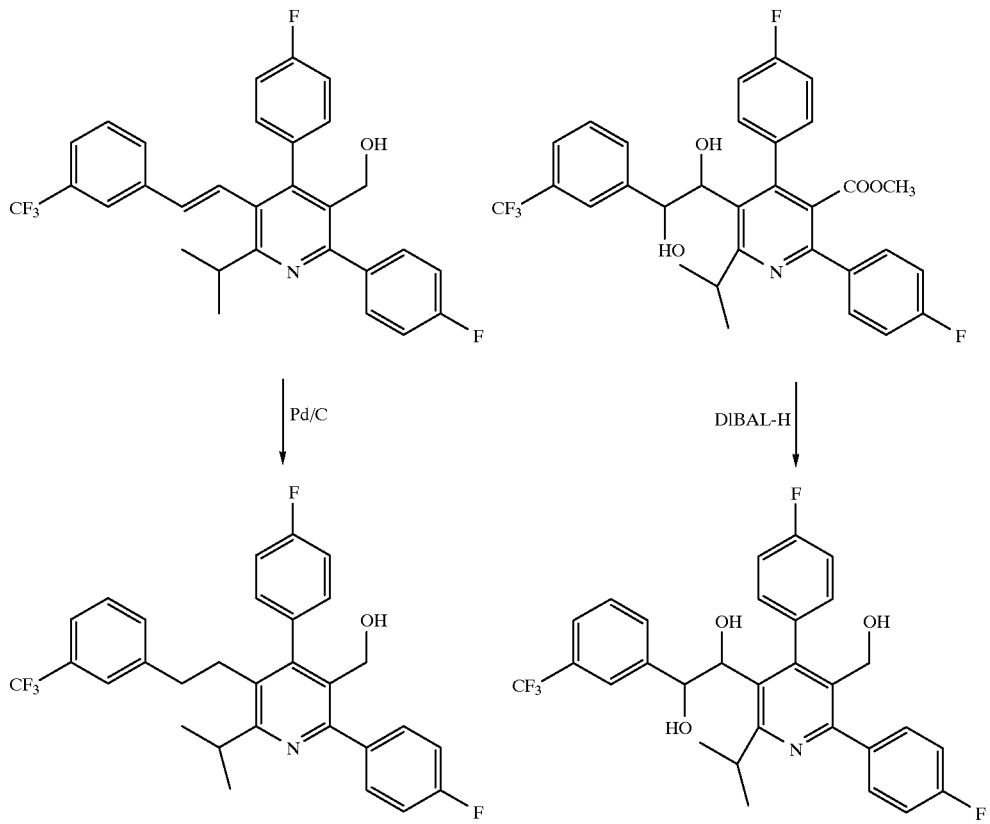

Suitable solvents are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

Suitable organometallic reagents are, for example, Grignard systems such as Mg/bromobenzotrifluoride and p-trifluoromethylphenyllithium. The system Mg/bromobenzotrifluoride is preferred.

The reductions and the derivatizations are carried out according to the above-mentioned methods.

The reductions are in general carried out in ethers, such as, for example, dioxane, tetrahydrofuran or diethyl ether or in hydrocarbons such as, for example, benzene, hexane or toluene. Toluene and tetrahydrofuran are preferred.

Suitable reducing agents are complex metal hydrides, such as, for example, lithium aluminium hydride, sodium cyanoborohydride, sodium aluminium hydride, diisobutylaluminium hydride, dimethoxymethylaluminate sodium salt or sodium bis-(2-methoxyethoxy)dihydroaluminate (Red-Al). Diisobutylaluminium hydride (DIBAL-H) and dimethoxymethylaluminate sodium salt are preferred.

The reducing agent is in general employed in an amount from 4 mol to 10 mol, preferably from 4 mol to 5 mol, relative to 1 mol of the compounds to be reduced.

The reduction in general proceeds in a temperature range from −78° C. to +50° C., preferably from −78° C. to 0° C., particularly preferably at −78° C., in each case depending on the choice of the reducing agent and solvent.

The reduction in general proceeds at normal pressure, but it is also possible to work at elevated or reduced pressure.

The reductions can however also be carried out using reducing agents which are suitable for the reduction of ketones to hydroxy compounds. Particularly suitable in this case is reduction with metal hydrides or complex metal hydrides in inert solvents, if appropriate in the presence of a trialkylborane. Preferably, the reduction is carried out using complex metal hydrides such as, for example, lithium borohydride, sodium borohydride, potassium borohydride, zinc borohydride, lithium trialkylborohydride or lithium aluminium hydride. The reduction is very particularly preferably carried out using sodium borohydride, in the presence of triethylborane.

The hydrogenation is carried out by customary methods using hydrogen in the presence of noble metal catalysts, such as, for example, Pd/C, Pt/C or Raney nickel in one of the abovementioned solvents, preferably in alcohols such as, for example, methanol, ethanol or propanol, in a temperature range from −20° C. to +100° C., preferably from 0° C. to +50° C., at normal pressure or elevated pressure.

Derivatizations which may be mentioned by way of example are the following types of reaction:

oxidations, reductions, hydrogenations, halogenation, Wittig/Grignard reactions and amidations/sulphoamidations.

Possible bases for the individual steps are the customary strongly basic compounds. These preferably include organolithium compounds such as, for example, N-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride. N-Butyllithium and sodium hydride are particularly preferably employed.

Suitable bases are additionally the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate. Sodium hydroxide and potassium hydroxide are particularly preferably employed.

Suitable solvents for the individual reaction steps are also alcohols such as methanol, ethanol, propanol, butanol or tert-butanol. tert-Butanol is preferred.

It may be necessary to carry out some reaction steps under a protective gas atmosphere.

The halogenations are in general carried out in one of the abovementioned chlorinated hydrocarbons, methylene chloride being preferred.

Suitable halogenating agents are, for example, diethylaminosulphur trifluoride (DAST) or $SOCl_2$.

The halogenation in general proceeds in a temperature range from $-78°$ C. to $+50°$ C., preferably from $-78°$ C. to $0°$ C., particularly preferably at $-78°$ C., in each case depending on the choice of the halogenating agent and solvent.

The halogenation in general proceeds at normal pressure, but it is also possible to work at elevated or reduced pressure.

Suitable Wittig reagents are the customary reagents. 3-Trifluoromethylbenzyltriphenylphosphonium bromide is preferred.

Suitable bases are in general one of the abovementioned bases, preferably Li bis-(triethylbutyl)amide.

The base is employed in an amount from 0.1 mol to 5 mol, preferably from 0.5 mol to 2 mol, in each case relative to 1 mol of the starting compound.

The reaction with Wittig reagents is in general carried out in a temperature range from $0°$ C. to $150°$ C., preferably at $25°$ C. to $40°$ C.

The Wittig reactions are in general carried out at normal pressure. However, it is also possible to carry out the process at reduced pressure or at elevated pressure (e.g. in a range from 0.5 to 5 bar).

The compounds of the general formula (II) are known or can be prepared by oxidizing compounds of the general formula (IV)

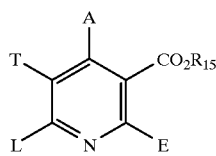

(V)

in which

A, E and L have the meaning indicated above, $R^{13}$ and $R^{14}$ are identical or different and represent straight-chain or branched alkyl having up to 4 carbon atoms, with oxidizing agents in inert solvents and in a second step selectively reducing the alkoxycarbonyl function ($CO_2R^{13}$) to the hydroxy function.

Suitable solvents for the oxidation are ethers such as diethyl ether, dioxane, tetrahydrofuran, glycol dimethyl ether, or hydrocarbons such as benzene, toluene, xylene, hexane, cyclohexane or petroleum fractions, or halohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

Suitable oxidizing agents are, for example, 2,3-dichloro-5,6-dicyano-benzoquinone, pyridinium chlorochromate (PCC), osmium tetroxide and manganese dioxide. 2,3-Dichloro-5,6-dicyano-benzoquinone (DDQ) is preferred for the abovementioned step.

The oxidizing agent is employed in an amount from 1 mol to 10 mol, preferably from 2 mol to 5 mol, relative to 1 mol of the compounds of the general formula (IV).

The oxidation in general proceeds in a temperature range from $-50°$ C. to $+100°$ C., preferably from $0°$ C. to room temperature.

The oxidation in general proceeds at normal pressure. However, it is also possible to carry out the oxidation at elevated or reduced pressure.

The 1,4-dihydropyridine-3,5-dicarboxylic acid esters of the general formula (IV) are known or can be prepared by known methods.

The compounds of the general formula (III) are for the most part new and are prepared by converting compounds of the general formula (V)

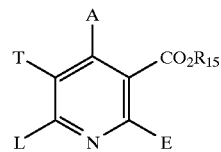

(V)

in which

A, E, L and T have the meaning indicated above and $R^{15}$ represents straight-chain or branched alkoxycarbonyl having up to 3 carbon atoms, first by reduction of the alkoxycarbonyl function into the compounds of the general formula (Ia)

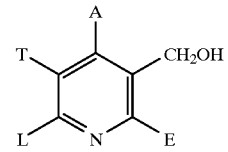

(Ia)

in which

A, E, L and T have the meaning indicated above, and in a second step oxidizing the hydroxymethyl function under the abovementioned conditions, preferably using pyridinium chlorochromate (PCC), to the aldehyde.

The individual reaction steps are in general carried out in a temperature range from $-10°$ C. to $+160°$ C., preferably from $0°$ C. to $+100°$ C. and normal pressure.

The compounds of the general formula (V) are prepared in analogy to the method described above for the preparation of the compounds of the general formula (II).

The compounds of the general formula (Ia) are new and can be prepared as described above.

The compounds of the general formulae (I) and (Ia) according to the invention have an unforeseeable spectrum of pharmacological action.

The compounds of the general formulae (I) and (Ia) according to the invention have useful pharmacological properties which are superior in comparison with the prior art, in particular they are highly effective inhibitors of cholesterol ester transfer protein (CETP) and stimulate reverse cholesterol transport. Reactive compounds according to the invention cause a lowering of the LDL cholesterol level in the blood with simultaneous raising of the HDL cholesterol level. They can therefore be employed primary and for the treatment of hyperlipoproteinaemia, hypolipoproteinaemia, dislipidaemia, hypotriglyceridaemia, combined hyperlipidaemia or arteriosclerosis.

The invention additionally relates to the combination of 2-aryl-substituted pyridines of the general formula (I) according to the invention with a glucosidase and/or amylase inhibitor for the treatment of familial hyperlipidaemias, obesity (adiposity) and diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

Furthermore, the invented compounds will be used in combination with cholesterol-lowering vastatins or ApoB-lowering drugs, to treat dyslipidemia, combined hyperlipidemia, hypercholesterolemia or hypertriglyceridemia. The mentioned combinations are also valid for primary or secondary prevention of coronary artery disease.

Vastatins as covered by the inventions are for instance lovastatin, simvastatin, pravastatin, fluvastatin, atorvastatin or cerivastatin, ApoB lowering compounds could be MTP-inhibitors.

The combinations of cerivastin or ApoB-Inhibitors with one of the above mentioned compounds with the formula (I) are most favored.

The pharmacological action of the substances according to the invention was determined in the following test:

CETP inhibition testing

1. Obtainment of CETP

CETP is obtained in partially purified form from human plasma by differential centrifugation and column chromatography and used for the test. To this end, human plasma is adjusted to a density of 1.21 g per ml using NaBr and centrifuged at 4° C. for 18 h at 50,000 rpm. The bottom fraction (d>1.21 g/ml) is applied to a Sephadex®phenyl-sepharose 4B (Pharmacia) column, washed with 0.15M NaCl/0.001M trisHCl pH 7.4 and then eluted with dist. water. The CETP-active fractions are pooled, dialysed against 50 mM Na acetate pH 4.5 and applied to a CM-Sepharose® (Pharmacia) column. The column is then eluted using a linear gradient (0–1M NaCl). The pooled CETP fractions are dialysed against 10 mM trisHCl pH 7.4 and then further purified by chromatography on a Mono Q® column (Pharmacia).

2. Obtainment of radiolabelled HDL 50 ml of fresh human EDTA plasma is adjusted to a density of 1.12 using NaBr and centrifuged for 18 h at 50,000 rpm at 4° C. in a Ty 65 rotor. The upper phase is used to obtain cold LDL. The lower phase is dialysed against 3×4 l of PDB buffer (10 mM tris/HCl pH 7.4, 0.15 mM NaCl, 1 mM EDTA, 0.02% $NaN_3$). 20 $\mu$l of $^3$H-cholesterol (Dupont NET-725; 1 $\mu$C/$\mu$l dissolved in ethanol) are then added per 10 ml of retentate volume and incubation is carried out at 37° C. under $N_2$ for 72 h.

The mixture is then adjusted to the density 1.21 using NaBr and centrifuged at 20° C. at 50,000 rpm in the Ty 65 rotor for 18 h. The upper phase is recovered and the lipoprotein fractions are purified by gradient centrifugation. To this end, the isolated, labelled lipoprotein fraction is adjusted to a density of 1.26 using NaBr. Each 4 ml of this solution are covered with a layer of 4 ml of a solution of density 1.21 and 4.5 ml of a solution of density 1.063 (density solutions of PDB buffer and NaBr) in centrifuge tubes (SW 40 rotor) and then centrifuged in the SW 40 rotor for 24 h at 38,000 rpm and 20° C. The intermediate layer containing the labelled HDL lying between the densities 1.063 and 1.21 is dialyzed against 3×100 volumes of PDB buffer at 4° C.

The retentate contains radiolabelled $^3$H-CE-HDL which, adjusted to about $5 \times 10^6$ cpm per ml, is used for the test.

3. Test procedure

For testing the CETP activity, the transfer of $^3$H-cholesterol ester from human HD lipoproteins to biotinylated LD lipoproteins is measured.

The reaction is ended by addition of streptavidin-SPA® beads (Amersham) and the transferred radioactivity is determined directly in a liquid scintillation counter.

In the test mixture, 10 $\mu$l of HDL-$^3$H-cholesterol ester (~50,000 cpm) are incubated at 37° C. for 18 h with 10 $\mu$l of biotin-LDL (Amersham) in 50 mM Hepes/0.15 m NaCl/0.% bovine serum albumin/0.05% $NaN_3$ pH 7.4 with 10 $\mu$l of CETP (1 mg/ml) and 3 $\mu$l of solution of the substance to be tested (dissolved in 10% DMSO/1% RSA). 200 $\mu$l of the SPA-streptavidin bead solution (Amersham TRKQ 7005) are then added, the mixture is incubated further for 1 h with shaking and then measured in the scintillation counter. As controls, corresponding incubations with 10 $\mu$l of buffer, 10 $\mu$l of CETP at 4° C. and 10 $\mu$l of CETP at 37° C. are used. The activity transferred into the control mixtures with CETP at 37° C. is rated as 100% transfer. The substance concentration at which this transfer is reduced by half is indicated as the $IC_{50}$ value.

In the following table, the $IC_{50}$ values (mol/l) are indicated for CETP inhibitors:

| Example no. | $IC_{50}$ value (mol/l) |
|---|---|
| 3 | $8 \times 10^{-7}$ |
| 14 | $7 \times 10^{-8}$ |
| 26 | $9 \times 10^{-7}$ |
| 31 | $5 \times 10^{-7}$ |
| 37 | $3 \times 10^{-7}$ |
| 42 | $1.7 \times 10^{-7}$ to $9 \times 10^{-8}$ |
| 45 | $3 \times 10^{-7}$ |
| 51 | $4 \times 10^{-7}$ |
| 53 | $1.7 \times 10^{-7}$ |
| 63 | $1.0 \times 10^{-6}$ |
| 68 | $8 \times 10^{-8}$ |
| 83 | $5 \times 10^{-6}$ |

Syrian golden hamsters from in-house breeding are anaesthetized after fasting for 24 hours (0.80 mg/kg of atropine, 0.80 mg/kg of Ketavet® s.c. 30' later 50 mg/kg of Nembutal i.p.). The jugular vein is then exposed and cannulated. The test substance is dissolved in a suitable solvent (as a rule Adalat placebo solution: 60 g of glycerol, 100 ml of $H_2O$, PEG-400 to 1000 ml) and administered to the animals via a PE catheter inserted into the jugular vein. The control animals receive the same volume of solvent without test substance. The vein is then tied off and the wound is closed. After various times—up to 24 hours after administration of the test substance—blood (about 250 µl) is removed from the animals by puncture of the retro-orbital venous plexus. Clotting is concluded by incubation at 4° C. overnight, then centrifugation is carried out at 6000 g for 10 minutes. In the serum thus obtained, the content of cholesterol and triglycerides is determined with the aid of modified commercially available enzyme tests (cholesterol enzymatic 14366 Merck, triglycerides 14364 Merck). Serum is suitably diluted using physiological saline solution.

100 µl of serum dilution are mixed with 100 µl of test substance in 96-well plates and incubated at room temperature for 10 minutes. The optical density is then determined at a wavelength of 492 nm using an automatic plate-reading apparatus (SLT Spectra). The triglyceride/cholesterol concentration contained in the samples is determined with the aid of a standard curve measured in parallel.

The determination of the content of HDL cholesterol is carried out after precipitation of the ApoB-containing lipoproteins by means of a reagent mixture (Sigma 352-4 HDL cholesterol reagent) according to the manufacturer's instructions.

In experiments to determine the oral activity, test substance dissolved in DMSO and suspended in 0.5% Tylose is administered orally by means of stomach tube to Syrian golden hamsters from in-house breeding. The control animals receive identical volumes of solvent without test substance. Feed is then withdrawn from the animals and at various times—up to 24 hours after substance administration—blood is removed by puncture of the retro-orbital venous plexus. Further processing is carried out as described above.

Determination of the CETP activity

After intravenous administration of 20 mg/kg of the compound from Example 42, an about 50% reduction of the CETP activity measured ex vivo is found over a period of at least 2 hours. 24 hours after substance administration, the HDL cholesterol values in the substance-treated group are about 30% higher than in the control group. Likewise, 24 hours after administration of 100 mg/kg per os of the compound from Example 42, HDL cholesterol levels which are increased by 30% are found in the substance-treated group.

After administration of 2×45 mg/kg per os of the compound from Example 44, the level of HDL cholesterol 24 hours after the first administration is increased by 20% compared with the control group. At this time, the level of the triglycerides is lowered by 70% compared with the control group.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if water is used as a diluent, organic solvents can optionally be used as auxiliary solvents.

Administration takes place in the customary manner, intravenously, parentally, perligually or orally, preferably orally.

In the case of parenteral administration, solutions of the active compound using suitable liquid excipient materials can be employed.

In general, it has proved advantageous in the case of intravenous administration to administer amounts of approximately 0.001 to 1 mg/kg, preferably approximately 0.01 to 0.5 mg/kg of body weight to achieve effective results, and in the case of oral administration the dose is approximately 0.01 to 20 mg/kg, preferably 0.1 to 10 mg/kg of body weight.

In spite of this, it may, if appropriate, be necessary to depart from the amounts mentioned, mainly depending on the body weight or on the type of administration route, on individual behaviour towards the medicament, the manner of its formulation and the time or interval at which administration takes place. Thus in some cases it may be adequate to manage with less than the abovementioned minimum amount, while in other cases the upper limit mentioned has to be exceeded. In the case of the administration of relatively large amounts, it may be advisable to divide these into several individual doses over the course of the day.

I. Eluents for TLC
$A_1$=petroleum ether 40/60: ethyl acetate 4:1
$A_2$=petroleum ether 40/60: ethyl acetate 6:1
$A_3$=petroleum ether 40/60: ethyl acetate 9:1
$A_4$=toluene
$A_5$=toluene : ethyl acetate 9:1
$A_6$=petroleum ether 40/60 : ethyl acetate 2:1
$A_7$=petroleum ether : ethyl acetate 5:1
$A_8$=toluene : ethyl acetate 7:3
$A_9$=cyclohexane/tetrahydrofuran 8:2
$A_{10}$=cyclohexane/tetrahydrofuran 9:1
$A_{11}$=toluene: ethyl acetate 8:2

STARTING COMPOUNDS

Example I

3-Methyl 5-ethyl 1,4-dihydro-2,4-di-(4-fluorophenyl)-6-isopropylpyridine- 3,5-dicarboxylate

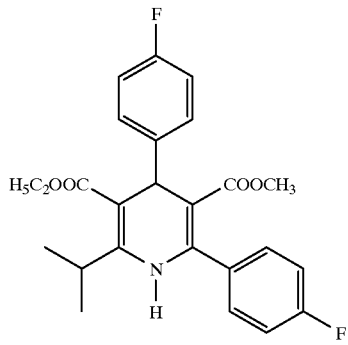

31 g (0.25 mol) of p-fluorobenzaldehyde, 49 g (0.25 mol) of methyl 4-fluorobenzoylacetate and 39.25 g (0.25 mol) of ethyl 3-amino-4-methyl-pent-2-enoate are boiled under reflux for 18 hours in 150 ml of ethylene glycol at a bath temperature of 130° C. The mixture is cooled to room temperature, extracted three times using 300 ml of diethyl ether, the combined ether phases are concentrated, and the residue is dissolved in 100 ml of toluene and chromatographed on 700 ml of silica gel (0.04–0.063 mm) using toluene as an eluent.

Yield: 21.52 g (19.5% of theory)

$R_f$=0.29 ($A_5$)

Example II

3-Methyl 5-ethyl 2,4-di-(4-fluorophenyl)-6-isopropyl-pyridine-3,5-dicarboxylate

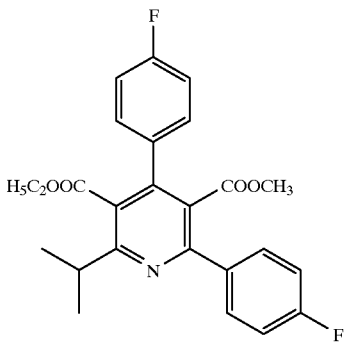

3.08 g (13.59 mmol) of 2,3-dichloro-5,6-dicyano-p-benzoquinone (DDQ) are added to a solution of 6.0 g (13.59 mmol) of the compound from Example I in 180 ml of $CH_2Cl_2$ p.a. and the mixture is stirred at room temperature for 1 h. The solid is then filtered off with suction through silica gel 60, washed with 200 ml of $CH_2Cl_2$, and the combined filtrates are concentrated to give an oil, which is crystallized in petroleum ether.

Yield: 3.96 g (66.3% of theory)

$R_f$=0.54 ($A_5$)

Example III

Methyl 2,4-di-(4-fluorophenyl)-6-isopropyl-5-hydroxymethyl-pyridine-3-carboxylate

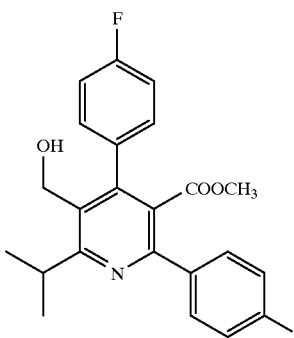

Under argon, 47.5 ml (0.166 mol, 2.05 eq.) of a 3.5-molar solution of sodium bis-(2-methoxyethoxy)-dihydroaluminate (Red-Al) in toluene are slowly added to a solution of 34.5 g (0.0811 mol) of the compound from Example II in 300 ml of THF p.a. and the mixture is stirred for 3 h. The reaction solution is treated with ice-cooling with 150 ml of a 20% strength potassium sodium tartrate solution and extracted with 200 ml of ethyl acetate. The organic phase is washed once with saturated NaCl solution, dried over $Na_2SO_4$ and concentrated in vacuo. The residue is chromatographed on silica gel 60, first with toluene, then with an increasing proportion of ethyl acetate (toluene/ethyl acetate=9:1). The eluates are concentrated and crystallized by triturating with petroleum ether.

Yield: 12.8 g (39.8% of theory)

$R_f$=0.29 ($A_5$)

Example IV

Methyl 2,4-di-(4-fluorophenyl)-6-isopropyl-5-formylpyridine-3-carboxylate

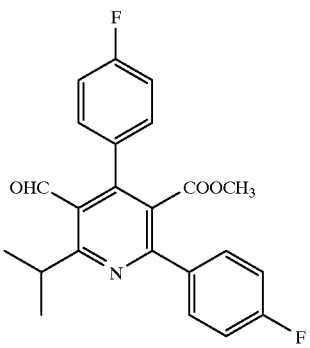

15.55 g (0.1525 mol; 2.0 eq.) of neutral $Al_2O_3$ and 32.93 g (0.1525 mol; 2 eq.) of pyridinium chlorochromate (PCC) are added to a solution of 30.3 g (0.0762 mol) of the compound from Example III in 500 ml of $CH_2Cl_2$ and the mixture is stirred at room temperature for 1 h. The solid is filtered off with suction through silica gel and washed with 600 ml of $CH_2Cl_2$, and the filtrate is concentrated in vacuo, the product crystallizing out.

Yield: 13.9 g (90.1% of theory)

$R_f$=0.8 ($A_{11}$)

Example V

Methyl 4,6-bis-p-fluorophenyl-2-isopropyl-3-[(p-trifluoromethylphenyl)-hydroxymethyl]-pyridine-5-carboxylate

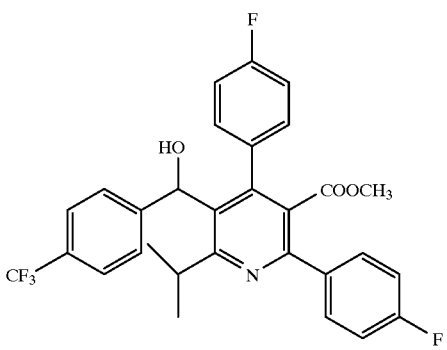

215.8 mg (8.88 mmol) of magnesium turnings are initially introduced into 30 ml of THF p.a., the mixture is heated to reflux under argon and 1.34 ml (9.56 mmol; 1.4 eq.) of 4-bromobenzodifluoride are rapidly added dropwise by means of a syringe. After an initially very violent reaction, the mixture is boiled under reflux for 30 min, it is then allowed to cool to room temperature (Grignard reagent). 2.7 g (6.83 mmol) of the compound from Example IV are dissolved in 20 ml of THF p.a., the solution is cooled to −78°

C. under argon and then the Grignard reagent is added by means of a syringe. The mixture is then stirred for 45 min without cooling. The reaction solution is partitioned in 250 ml of ethyl acetate/NH$_4$Cl solution (1:1), the organic layer is separated off and the aqueous layer is extracted twice with ethyl acetate. The combined organic phases are dried over Na$_2$SO$_4$ and concentrated in vacuo. The oily residue is crystallized using petroleum ether, filtered off with suction and dried in vacuo.

Yield: 2.55 g (69% of theory)

R$_f$=0.42 (A$_5$)

Example VI

Methyl 2,4-di-(4-fluorophenyl)-6-isopropyl-5-[4-(trifluorophenyl)-fluoromethyl]-pyridine-3-carboxylate

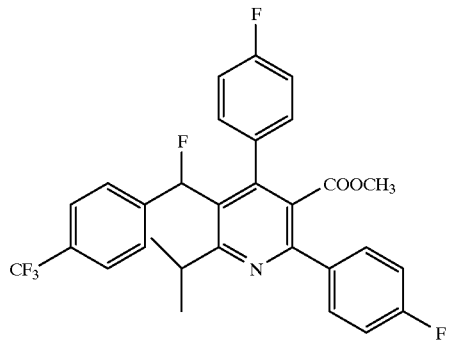

0.22 ml (1.66 mmol, 1.5 eq.) of diethylaminosulphur trifluoride (DAST) are added at −70° C. under argon to a solution of 600 mg (1.108 mmol) of the compound from Example V in 15 ml of CH$_2$Cl$_2$ p.a. by means of a syringe, the cooling bath is removed and the mixture is stirred at −5° C. for 1 h. The reaction solution is then partitioned in ethyl acetate/NH$_4$Cl solution, the organic phase is separated off and the aqueous phase is washed once with ethyl acetate. The combined ethyl acetate phases are dried over Na$_2$SO$_4$ and concentrated in vacuo, and the residue is crystallized by triturating with petroleum ether.

Yield: 359 mg (59.6% of theory)

R$_f$=0.79 (A$_5$)

Example VII

Methyl 2,4-di-(4-fluorophenyl)-6-isopropyl-5-[4-(trifluorophenyl)-chloromethyl]-pyridine-3-carboxylate

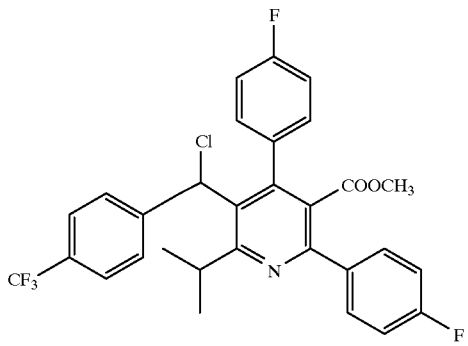

1.85 g (3.416 mmol) of the compound from Example V are dissolved in 500 ml of CH$_2$Cl$_2$ p.a. under argon and cooled to −40° C., and 0.745 ml (10.25 mmol; 3.0 eq.) of SOCl$_2$ are added dropwise by means of a syringe. The mixture is stirred for a further 30 min at −40° C. and the mixture is then stored at −30° C. overnight. It is then stirred further at room temperature (35 min) until conversion is complete (TLC). The mixture is poured onto 100 ml of saturated NaHCO$_3$ solution and 200 ml of ethyl acetate, the organic phase is separated off, washed once with 50 ml of saturated NaHCO$_3$ solution, dried over Na$_2$SO$_4$ and concentrated in vacuo, and the residue is crystallized by triturating with petroleum ether.

Yield: 1.42 g (74.6% of theory)

R$_f$=0.9 (A$_5$)

Example VIII

Methyl 2,4-di-(4-fluorophenyl)-6-isopropyl-5-[4-(trifluorophenyl)-azidomethyl]-pyridine-3-carboxylate

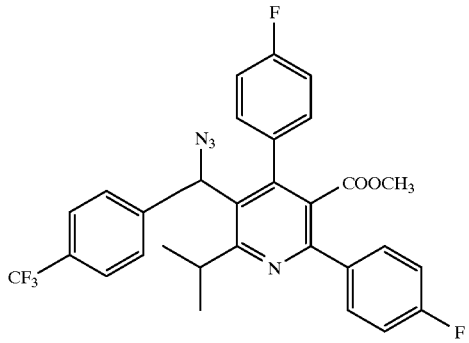

0.9 g (1.607 mmol) of the compound from Example VII and 1.044 g (16.07 mmol; 10 eq.) of NaN$_3$ are stirred in 40 ml of DMSO for 4 h at 80° C. and then for 12 h at room temperature. 100 ml of ethyl acetate are then added, and the mixture is washed once with water and three times with saturated NaCl solution. The organic phase is dried over Na$_2$SO$_4$ and concentrated, and the residue is crystallized by triturating with petroleum ether.

Yield: 370 mg (40.7% of theory)

$R_f = 0.81$ (A$_5$)

Example IX

Methyl 2,4-di-(4-fluorophenyl)-6-isopropyl-5-[4-(trifluoromethylphenyl)-aminomethyl]-pyridine-3-carboxylate

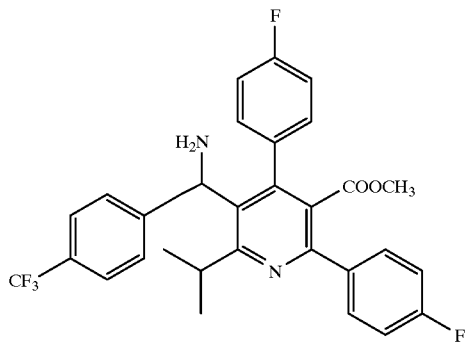

630 mg (1.112 mmol) of the compound from Example VIII are hydrogenated overnight at normal pressure and 20° C. using hydrogen in 40 ml of abs. CH$_3$OH and 20 ml of abs. THF in the presence of 60 mg of Pd/C (10%). The catalyst is then filtered off with suction through silica gel and washed with methanol/THF (1:1) and THF, and the solvent is distilled off in vacuo. The residue is purified on 70 g of silica gel by column chromatography using toluene and toluene/ethyl acetate (7:3).

Yields: 1st fraction=113 mg (18.8% of theory) 2nd fraction=296 mg (49.3% of theory)

$R_f = 0.13$ (A$_5$)

Example X

Methyl 2,4-di-(4-fluorophenyl)-6-cyclopentyl-5-[2-(benzothiazol-2-yl)-hydroxymethyl]-pyridine-3-carboxylate

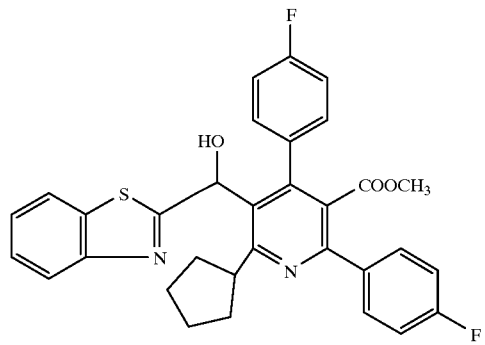

1.04 ml (1.7 mmol) of butyllithium (1.6 molar in hexane) are added under argon at −78° C. to 230 mg (1.7 mmol) of benzothiazole in 20 ml of THF p.a. After stirring for 5 min at −78° C., a solution of 623 mg (1.478 mol) of methyl 2,4-di-(4-fluorophenyl)-6-cyclopentyl-5-formyl-pyridine-3-carboxylate in 10 ml of THF p.a. is added dropwise. The temperature is then allowed to climb from −78° C. to room temperature. The mixture is poured onto ethyl acetate/NH$_4$Cl solution with ice-cooling, and the organic phase is washed once with saturated NaCl solution, dried over Na$_2$SO$_4$ and concentrated. After chromatography on 50 ml of silica gel using toluene, 466 mg (56.7% of theory) are obtained.

$R_f = 0.33$ (A$_5$)

Example XI

Methyl 2,4-di-(4-fluorophenyl)-6-cyclopentyl-5-[2-(benzothiazol-2-yl)-fluoromethyl]-pyridine-3-carboxylate

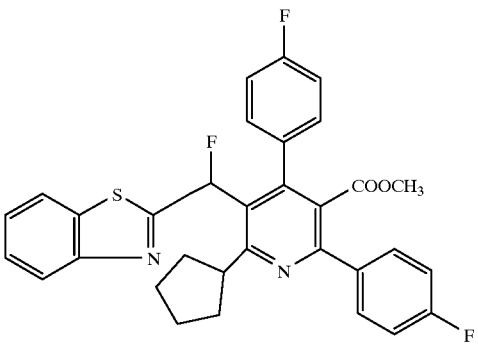

Analogously to Example VI, 439 mg (0.789 mmol) of the compound from Example X are reacted with 190.7 mg (1.183 mmol; 1.5 eq.) of DAST in 30 ml of CH$_2$Cl$_2$ p.a.

Yield: 350 mg (79.5% of theory)

$R_f = 0.47$ (A$_5$)

Example XII

Methyl 2,4-di-(4-fluorophenyl)-6-isopropyl-5-[2-(E/Z)-3-(trifluoromethyl-phenyl)vinyl-pyridine-3-carboxylate

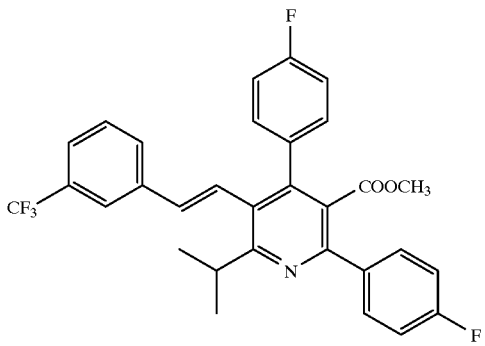

1.755 g (3.5 mmol) of 3-trifluoromethylbenzyl-triphenylphosphonium bromide are treated dropwise at 0° C. under argon in 10 ml of THF p.a. with 3.85 ml (3.85 mmol; 1.1 eq.) of lithium bis-(trimethylsilyl)amide (1.0 molar in hexane) in the course of 10 min and the mixture is stirred at 0° C. for 30 min. 1.246 mg (3.15 mmol; 0.9 eq.) of the compound from Example IV in 2 ml of THF are then added dropwise in 10 min at 0° C. and the mixture is stirred for 20 min at 0° C. and for 80 min without cooling. The reaction solution is treated with saturated NH$_4$Cl solution and extracted three times with 40 ml of ethyl acetate each time. The combined ester phases are dried over Na$_2$SO$_4$ and concentrated in vacuo. The residue is chromatographed on 60 ml of silica gel 60 using toluene.

Yield: 1.22 g (72.1% of theory)
$R_f=0.77$ ($A_4$)

Example XIII

Methyl 2,4-di-(4-fluorophenyl)-6-isopropyl-5-[2-(3-(trifluoromethyl-phenyl)-1,2-dihydroxyethyl]-pyridine-3-carboxylate

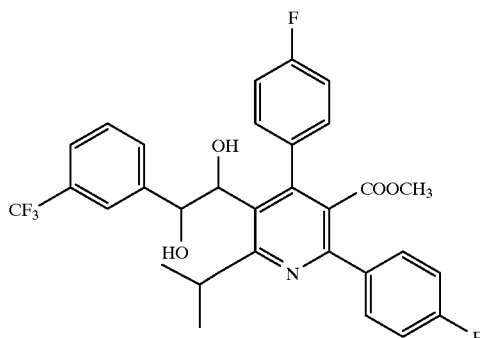

A mixture of 300 mg (0.559 mmol) of the compound from Example XII, 141 mg (1.2 mol; 2.1 eq) of N-methylmorpholine-N-oxide and 2.1 ml (0.168 mmol) of a 2.5% strength osmium tetroxide solution in tert-butanol ($\Delta 0.08$ mol of $OsO_4 \times 1^{-1}$) is stirred at room temperature overnight in the dark (mixture surrounded by means of aluminium foil). After addition of 130 mg (1 mmol) of $Na_2SO_3$, the reaction solution is diluted with 30 ml of $CH_2Cl_2$, 10 ml of NaCl solution and 10 ml of water. The $CH_2Cl_2$ phase is separated off, washed once with NaCl solution and water, dried over $Na_2SO_4$, filtered and concentrated. The oily residue is purified by chromatography on 50 ml of silica gel 60 using, toluene and toluene/ethyl acetate (8:2).

Yield: 140 mg (43.8% of theory)
$R_f=0.18$ ($A_5$)

Example XIV 4,6-Bis-p-fluorophenyl-2-isopropyl-3-(p-trifluoromethyl)-benzoyl-5-pyridinecarbaldehyde

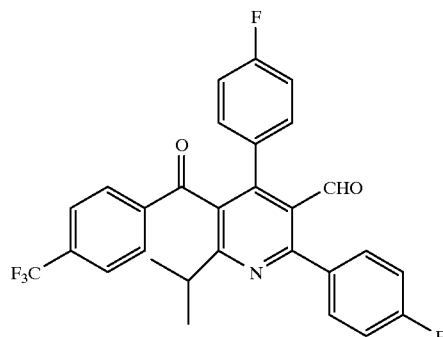

A solution of 1.3 g (2.5 mmol) of 4,6-bis-p-fluorophenyl-5-hydroxymethyl-2-isopropyl-3-[(p-trifluoromethylphenyl)-(hydroxy)-methyl]-pyridine in 50 ml of $CH_2Cl_2$ is treated at RT with a mixture of 1 g (10 mmol) of $Al_2O_3$ and 2.2 g (10 mmol) of PCC and stirred overnight at RT. For working-up, silica gel is added, the mixture is stirred at RT for 20 min, filtered through silica gel and washed with $CH_2Cl_2$, and the filtrate is concentrated.

Yield: 1.04 g (82% of theory)
$R_f=0.46$ (toluene)

Example XV 4,6-Bis-p-fluorophenyl-2-isopropyl-3-[{1-(4-fluoronaphthyl)}-(methoxy)methyl]-5-pyridinecarboxylate

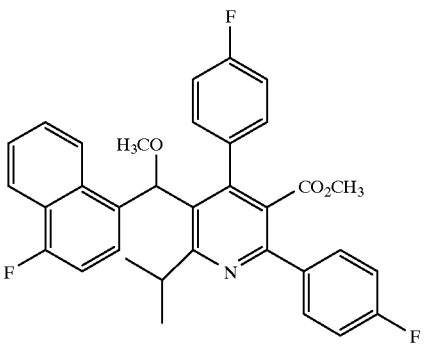

A solution of 1 g (1.8 mmol) of methyl 4,6-bis-p-fluorophenyl-2-isopropyl-3-[{1-(4-fluoronaphthyl}-(hydroxy)methyl]-5-pyridinecarboxylate in 10 ml of DMF is added dropwise under argon at $-10°$ C. to a suspension of 55 mg of NaH (80%) in 20 ml of DMF and the mixture is stirred for 20 min. A solution of 0.14 ml (2.3 mmol) of $CH_3I$ in 5 ml of DMF is then added dropwise at $-10°$ C. After stirring for 1 h, the mixture is slowly thawed and stirred at RT for 2 h. For working-up, it is treated with 20 ml of 1N AcOH, extracted three times with ethyl acetate, and the combined organic phases are dried over $Na_2SO_4$, filtered and concentrated. The product is chromatographed on silica gel 60.

Yield: 0.95 g (95% of theory)
$R_f=0.53$ (toluene)

Example XVI 4,6-Bis-p-fluorophenyl-2-isopropyl-3-[(p-trifluoromethyl-phenyl)(fluoro)methyl]5-pyrimidinecarbaldehyde

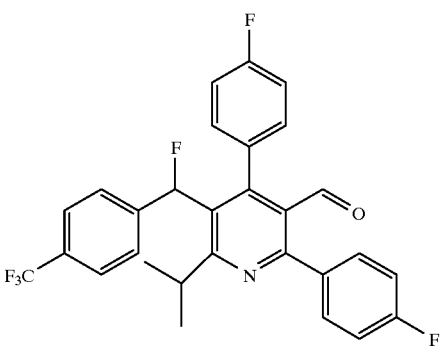

9.0 g (17.5 mmol) of the compound 2,4-di-(4-fluorophenyl)-6-isopropyl-5-[(p-trifluoromethylphenyl)-fluoromethyl]-3-hydroxymethyl-pyriline (Example 31) are stirred for 2 h at RT in 200 ml of $CH_2Cl_2$ with 3.56 g (34.9 mmol) of Al₂O₃ and 7.68 g (34.9 mmol) of PCC. Silica gel is then added, the mixture is stirred for 10 min and filtered through silica gel, the solid is washed with CH₂Cl₂ and the filtrate is concentrated.

Yield: 7.49 g (84% of theory)
R$_f$=0.76 (toluene)

Example XVII

Methyl 4,6-bis-p-fluorophenyl-2-isopropyl-3-[(p-trifluoromethylphenyl)-(fluoro)methyl ]-pyridine-5-ω-propenoate

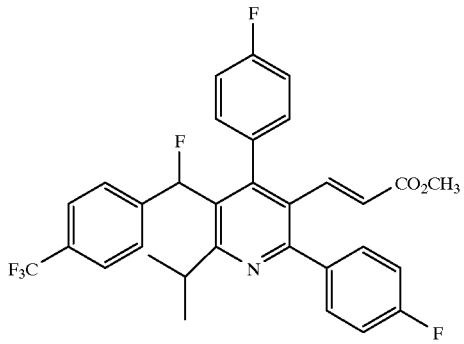

0.19 ml of diisopropylamine is treated at −78° C. in 10 ml of THF under argon with 0.78 ml of 1.6N (1.25 mmol) n-BuLi, and the mixture is stirred at 0° C. for 5 min, treated at −78° C. with 0.09 ml (1.1 mmol) of methyl acetate and stirred for 30 min. 0.40 g (0.78 mmol) of the compound from Example XVI dissolved in 10 ml of THF is then added dropwise. After stirring at −78° C. for 4 h, the mixture is thawed overnight. It is treated with NH₄Cl solution and water with cooling and extracted twice with ethyl acetate. The combined organic phases are dried over sodium sulphate, concentrated and chromatographed on silica gel 60 (petroleum ether/ethyl acetate=10:1).

Yield: 0.11 g (25% of theory)
R$_f$=0.35 (petroleum ether/ethyl acetate=9:1)

Example XVIII 4,6-Bis-p-fluorophenyl-2-isopropyl-3-p-trifluoromethylphenyl-benzoyl-5-pyridineacetaldehyde methyl enol ether

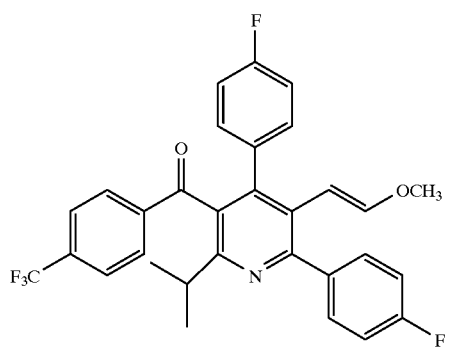

5.7 g (13.2 mmol) of methoxymethyl-triphenylphosphonium bromide/sodium amide (Instant Ylide) are suspended in 100 ml of THF, stirred at RT for 20 min, treated dropwise with a solution of 2.7 g (5.3 mmol) of the compound from Example XIV in 50 ml of THF and stirred overnight. For working-up, the mixture is added to ice-water, extracted three times with CH₂Cl₂, and the combined organic phases are dried, filtered, concentrated and chromatographed on silica gel 60 (petroleum ether/ethyl acetate=9:1).

Yield: 1.0 g (35% of theory)
R$_f$=0.6 (petroleum ether/ethyl acetate=9:1)

Example XIX 4,6-Bis-p-fluorophenyl-2-isopropyl-3-p-trifluoromethyl-benzoyl-5-pyridineacetaldehyde

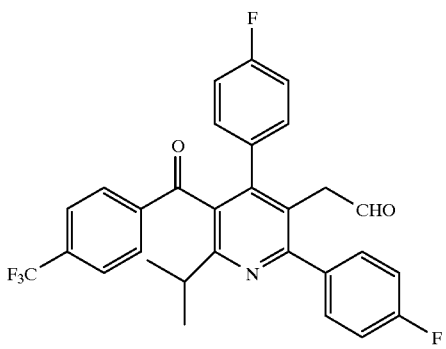

0.2 g (1.3 mmol) of NaI and 0.14 g (1.3 ml) of (CH₂)₃SiCl is added under argon to a solution of 0.7 g (1.3 mmol) of the compound from Example XVIII in 30 ml of CH₃CN and the mixture is stirred at RT for 3 h. After again adding the same amounts of NaI and Me₃SiCl, it is stirred overnight. The mixture is then treated with saturated aqueous Na₂SO₂O₃ solution and extracted three times with ether, and the combined organic phases are dried, concentrated and chromatographed on silica gel 60 (petroleum ether/ethyl acetate= 10:1).

Yield: 0.38 g (55% of theory)
R$_f$=0.55 (toluene)

PREPARATION EXAMPLES

Example 1

4,6-Bis-(p-fluorophenyl)-5-hydroxymethyl-2-isopropyl-3-[(p-trifluoromethylphenyl)-(hydroxy)-methyl]-pyridine

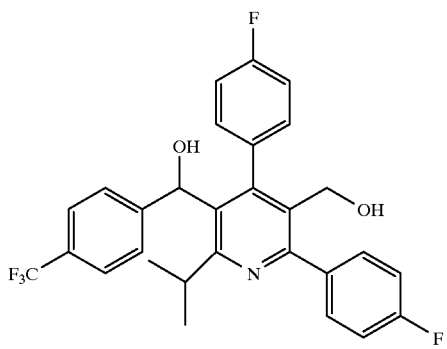

A solution of 2 g (3.7 mmol) of the compound from Example V in 10 ml of THF is added dropwise under argon at reflux to 11 ml of LiAlH₄ in THF (1 molar solution) and the mixture is stirred for 1 h. For working-up, it is cooled to 0° C., treated with 20% strength aqueous Na K tartrate solution, diluted with water and extracted three times with ethyl acetate. The combined organic phases are dried over Na₂SO₄, filtered and concentrated, and the product is chromatographed on silica gel 60 (toluene/ethyl acetate=9:1).

Yield: 1.38 g (73% of theory)

$R_f$=0.20 (toluene/ethyl acetate=9:1)

Example 2

4,6-Bis-(p-fluorophenyl)-5-hydroxymethyl-2-isopropyl-3-p-trifluoromethylbenzoylpyridine

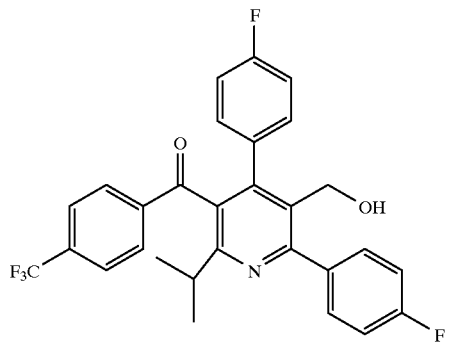

4 mg (0.10 mmol) of NaBH₄ are added at 0° C. to a suspension of 50 mg (0.1 mmol) of the compound from Example XIV in 10 ml of CH₃OH and, after addition of 2 ml of dioxane, the mixture is stirred for 1 h. For working-up, it is acidified with 1N AcOH and extracted three times with ethyl acetate, and the combined organic phases are dried over Na₂SO₄, filtered and concentrated.

Yield: 48.3 mg (94% of theory)

$R_f$=0.39 (CH₂Cl₂/CH₃OH=9:1)

Example 3

4,6-Bis-(p-fluorophenyl)-2-isopropyl-3-[(p-trifluoromethylphenyl)-(fluoro)methyl]5-(1-hydroxyethyl)pyridine

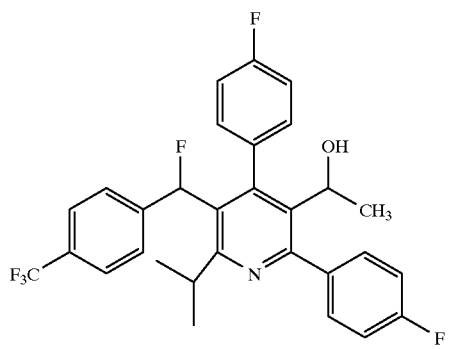

700 mg (1.36 mmol) of the compound from Example XVI are stirred under argon at −78° C. for 3 h with 0.54 ml (3M in THF, 1.63 mmol) of methylmagnesium bromide in 10 ml of THF. After addition of a further 0.27 ml of 3M (0.81 mmol) CH₃MgBr and stirring for 1 h, the mixture is warmed, stirred for 1 h, treated with saturated aqueous NH₄Cl solution and CH₂Cl₂, brought to pH 5 (1N HCl), shaken and separated. The aqueous phase is extracted again with CH₂Cl₂, and the combined organic phases are shaken with NaCl solution, dried over sodium sulphate and concentrated.

Yield: 0.72 g (99.9% of theory)

$R_f$=0.36 (toluene)

Example 4

4,6-Bis-(p-fluorophenyl)-2-isopropyl-3-[(p-trifluoromethylphenyl)-(fluoro)methyl]5-(3-hydroxy-1-propyl)pyridine

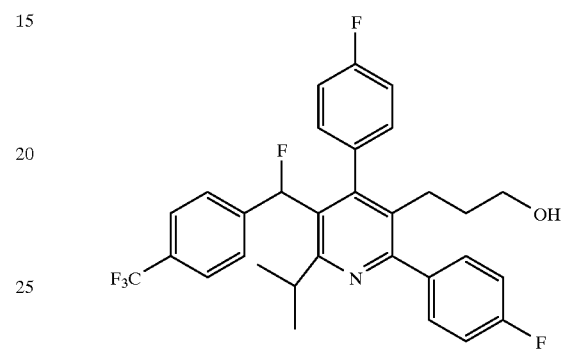

79 mg (0.14 mmol) of the compound from Example XVII are treated with 0.37 ml of 1M (0.37 mmol) LiAlH₄ solution in 4 ml of THF under argon at RT and the mixture is stirred for 30 min. It is then added to ice-water, adjusted to pH 3 using 1N HOAc and extracted three times with ethyl acetate. The combined organic phases are dried over sodium sulphate, filtered and concentrated, and the residue is chromatographed on silica gel 60 (petroleum ether/ethyl acetate= 3:1).

Yield: 0.034 g (46% of theory)

$R_f$=0.38 (petroleum ether 40:60: ethyl acetate=3:1)

Example 5

4,6-Bis-(p-fluorophenyl)-2-isopropyl-3-p-trifluoromethylbenzoyl-5-(2-hydroxy-1-ethyl)-pyridine

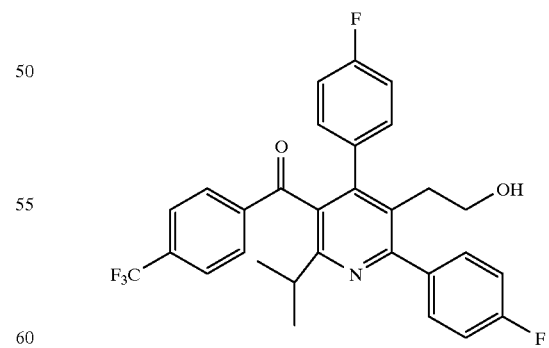

0.05 g (0.1 mmol) of the compound from Example XIX is suspended in 20 ml of EtOH and treated with 8 mg (0.2 mmol) of NaBH₄, and the mixture is stirred at RT for 2 h. It is then treated with water, adjusted to pH 5 (1N AcOH) and extracted three times with ethyl acetate. The combined organic phases are dried, concentrated and chromatographed on silica gel 60 (petroleum ether/ethyl acetate=3:1)

Yield: 0.03 g (65% of theory)

$R_f$=0.79 (petroleum ether/ethyl acetate=2:1)

The compounds listed in Tables 1–4 are prepared in analogy to the procedures of Examples 1–5:

TABLE 1

| Ex.-No. | T | Y | $R_f$ | Eluent |
|---|---|---|---|---|
| 6 | 4-(F₃C)-C₆H₄-CHF- | o-CH₃, p-F | 0,61 | A₁ |
| 7 | 4-(F₃C)-C₆H₄-CO- | o-CH₃, p-F | 0,53 | A₂ |
| 8 | 3-(F₃C)-C₆H₄-CO- | p-F | 0,51 | A₁ |
| 9 | 4-F-naphthyl-CHF- | p-F | 0,58 | A₁ |
| 10 | 4-F-naphthyl-CO- | p-F | 0,51 | A₁ |

TABLE 1-continued

| Ex.-No. | T | Y | $R_f$ | Eluent |
|---|---|---|---|---|
| 11 | 4-F-naphthyl-CH(OH)- | p-F | 0,27 | A₁ |
| 12 | 4-F-naphthyl-CH(OCH₃)- | p-F | 0,47 | A₁ |

TABLE 2

| Ex.-No. | T | Y | $R_f$ | Eluent |
|---|---|---|---|---|
| 13 | 4-(F₃C)-C₆H₄-CO- | p-F | 0,28 | A₃ |

TABLE 2-continued
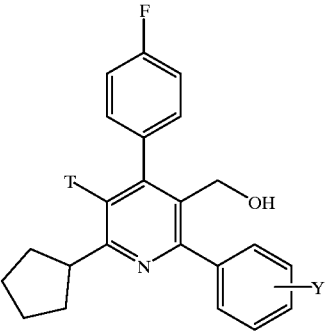
| Ex.-No. | T | Y | R_f | Eluent |
|---|---|---|---|---|
| 14 | 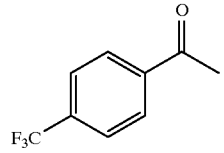 | m-CF₃ | 0,58 | A₁ |
| 15 | 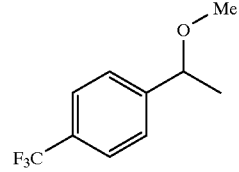 | p-F | 0,53 | A₁ |
| 16 | 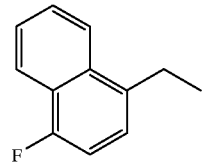 | m-CF₃ | 0,51 | A₁ |
| 17 | 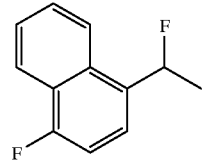 | m-CF₃ | 0,44 | A₁ |
| 18 | 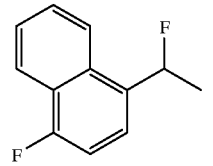 | p-F | 0,56 | A₁ |
| 19 | 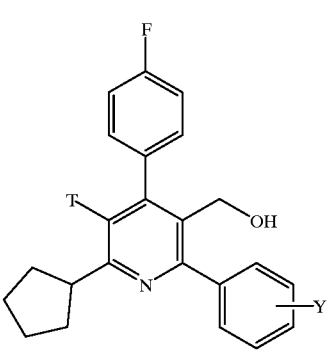 | m-CF₃ | 0,62 | A₁ |
TABLE 2-continued
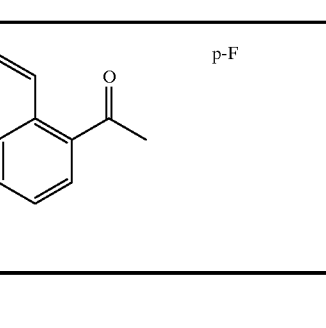
| Ex.-No. | T | Y | R_f | Eluent |
|---|---|---|---|---|
| 20 | 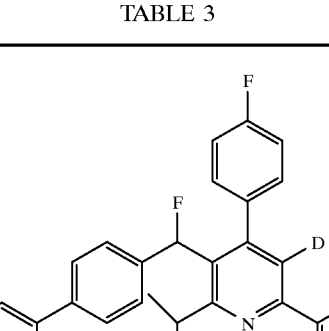 | p-F | 0,57 | A₁ |
TABLE 3
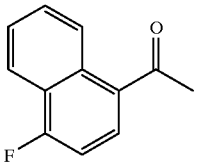
| Ex.-No. | D | R_f | Eluent |
|---|---|---|---|
| 21 | 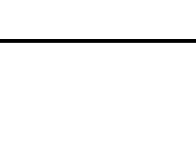 | 0,39 | A₄ |
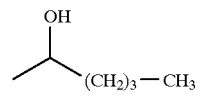

TABLE 4
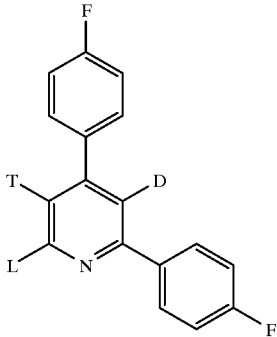
| Ex.-No. | T | L | D | $R_f$ | Eluent |
|---|---|---|---|---|---|
| 22 | 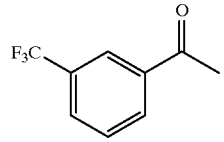 | iPr | ~~~OH | 0,37 | $A_1$ |
| 23 | 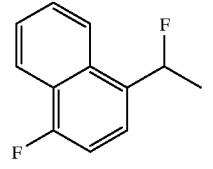 | iPr | ~~~OH | 0,35 | $A_5$ |
| 24 | 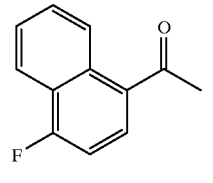 | iPr | ~~~OH | 0,64 | $A_6$ |
| 25 | 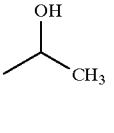 | iPr | OH / CH$_3$ | 0,28 | $A_2$ |
| 26 | 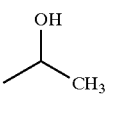 | cPent | OH / CH$_3$ | 0,60 | $A_1$ |
| 27 | 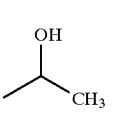 | iPr | OH / CH$_3$ | 0,51 | $A_1$ |
| 28 | 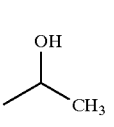 | iPr | OH / CH$_3$ | 0,28 | $A_3$ |

TABLE 4-continued

| Ex.-No. | T | L | D | $R_f$ | Eluent |
|---|---|---|---|---|---|
| 29 | 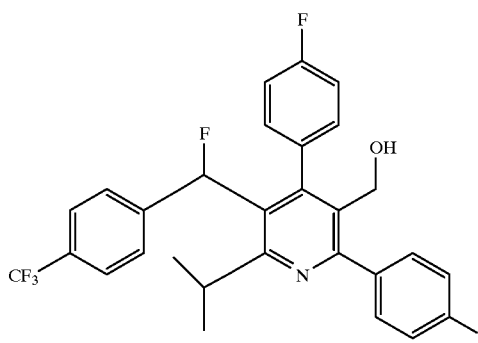 | iPr | OH–CH(CH₃) | 0,48 | $A_1$ |
| 30 | 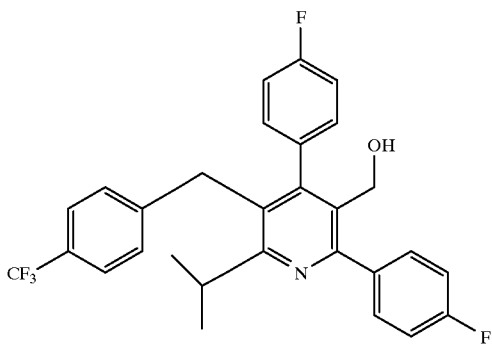 | cPent | OH–CH(CH₃) | 0,53 | $A_1$ |

Example 31

2-,4-di-(4-Fluorophenyl)-6-isopropyl-5-[4-(trifluoromethylphenyl)-fluoromethyl]-3-hydroxymethyl-pyridine Under argon, a mixture of 23.04 mg (0.607 mmol; 1.1 eq.) of LiAlH₄ and 5 ml of THF p.a. is warmed to 60° C. to 80° C. and 0.3 g (0.552 mmol) of the compound from Example VI dissolved in 5 ml of THF is allowed to run in dropwise. The mixture is then boiled under reflux for 1 h. After cooling to 0° C., 5 ml of a 20% strength potassium sodium tartrate solution and 10 ml of water are added and the mixture is extracted twice with 80 ml of ethyl acetate each time. The combined organic phases are washed once with saturated NaCl solution, dried over Na₂SO₄ and concentrated in vacuo. The residue is chromatographed on 60 g of silica gel 60 first using toluene and then using toluene/ethyl acetate (9:1).

Yield: 156 mg (54.9% of theory)
$R_f$=0.53 (toluene/ethyl acetate 9:1)

Example 32

2,4-di-(4-Fluorophenyl)-6-isopropyl-5-(4-(trifluoromethylbenzyl)-3-hydroxymethyl-pyridine 11.2 mg (0.295 mmol; 3.0 eq.) of LiAlH₄ are suspended under argon in 2 ml of THF p.a. at 80° C. 55 mg (0.0982 mmol) of the compound from Example VII in 2 ml of THF p.a. are added dropwise at 80° C. After stirring at 80° C. for 8 h, the solution is cooled to 20° C, treated with 5 ml of 20% strength potassium sodium tartrate solution, extracted twice with 20 ml of ethyl acetate and dried over $NA_2SO_4$, and the organic phase is concentrated. The residue is purified by silica gel chromatography using toluene.

Yield: 36 mg (73.0% of theory)

$R_f$=0.58 (toluene/ethyl acetate 9:1)

Example 33

2,4-di-(4-Fluorophenyl)-6-isopropyl-5-[4-(trifluoromethylphenyl)-aminomethyl]-3-hydroxymethyl-pyridine

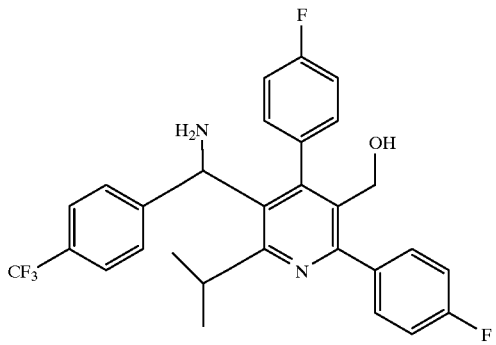

90 mg (0.167 mmol) of the compound from Example IX are dissolved under argon in 5 ml of toluene p.a. at −78° C. and 0.84 ml (1 mmol; 6 eq.) of diisobutylaluminium hydride (DIBAL-H; 1.2 molar in toluene) is added from a syringe. The mixture is stirred for a further 15 min at −78° C. and the reaction solution is then stored at −30° C. overnight. It is then cooled to −78° C., 2 ml of 20% strength potassium sodium tartrate solution are added and the mixture is diluted with toluene. The solution is washed once with saturated NaCl solution, dried over $Na_2SO_4$ and concentrated. The residue is purified by chromatography on silica gel (40 g) using toluene and toluene/ethyl acetate (8:2).

Yield: 60 mg (70.3% of theory)

$R_f$=0.27 ($A_{11}$)

Example 34

2,4-di-(4-Fluorophenyl)-6-cyclopentyl-5-[2-(benzothiazol-2-yl)-fluoromethyl]-3-hydroxymethyl-pyridine

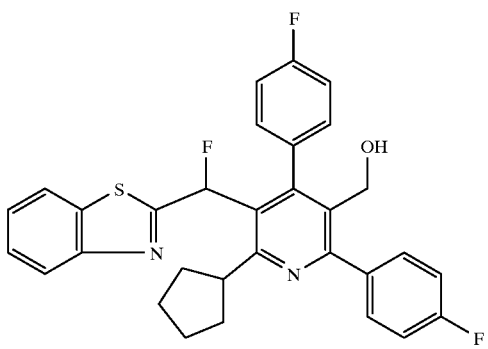

According to Example 31, 450 mg (0.9 mmol) of the compound from Example XI are reduced to the alcohol using 44.4 mg (1.171 mmol; 1.3 eq) of $LiAlH_4$ in 30 ml of THF.

Yield: 182 mg (42.6% of theory)

$R_f$=0.45 (toluene/ethyl acetate 9:1)

The compounds listed in Tables 5–8 are prepared according to the procedures indicated above:

TABLE 5

| Ex.-No. | E | $R^{18}$ | $Z^1/Z^2$ | L | $R_f$ (eluent) |
|---|---|---|---|---|---|
| 35 | 3-CF₃-phenyl | F | p-CF₃/H | isopropyl | 0,2 ($A_7$) |
| 36 | 4-Cl-phenyl | F | p-CF₃/H | isopropyl | 0,44 ($A_4$) |

TABLE 5-continued
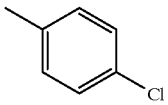
| Ex.-No. | E | $R^{18}$ | $Z^1/Z^2$ | L | $R_f$ (eluent) |
|---|---|---|---|---|---|
| 37 | 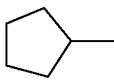 | F | p-CF$_3$/H | 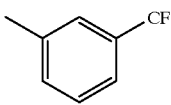 | 0,57 (A$_5$) |
| 38 | 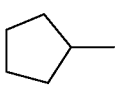 | F | p-CF$_3$/H | 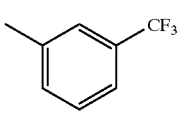 | 0,23 (A$_7$) |
| 39 | 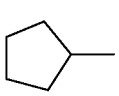 | H | p-CF$_3$/H | 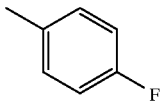 | 0,22 (A$_7$) |
| 40 | 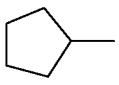 | F | 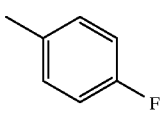 | 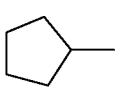 | 0,26 (A$_7$) |
| 41 | 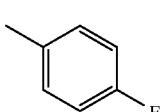 | H | p-CF$_3$/H | 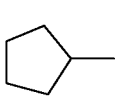 | 0,30 (A$_5$) |
| 42 Racemat | 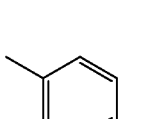 | F | p-CF$_3$/H |  | 0,6 (A$_5$) |
| 43 Enantiomer I | 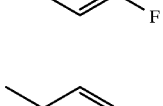 | F | p-CF$_3$/H |  | 0,6 (A$_5$) |
| 44 Enantiomer II | 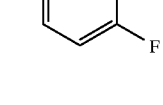 | F | p-CF$_3$/H |  | 0,6 (A$_5$) |
| 45 |  | F | p-CF$_3$O—/H |  | 0,41 (A$_5$) |

TABLE 5-continued
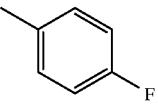
| Ex.-No. | E | R[18] | Z[1]/Z[2] | L | $R_f$ (eluent) |
|---|---|---|---|---|---|
| 46 | 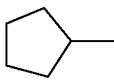 | F | o,p-(CF$_3$)$_2$ | 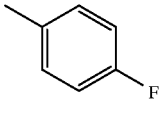 | 0,60 (A$_5$) |
| 47 | 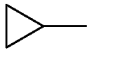 | F | p-CF$_3$/H | 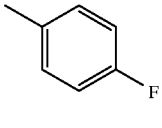 | 0,67 (A$_5$) |
| 48 | 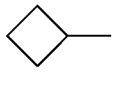 | F | p-CF$_3$/H | 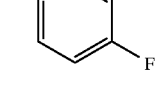 | 0,59 (A$_5$) |
| 49 |  | F | o,p(CF$_3$)$_2$ | 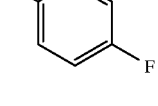 | 0,43 (A$_5$) |
| 50 | 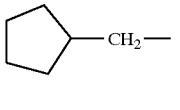 | F | p-CF$_3$/H | 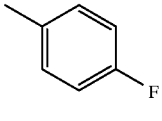 | 0,29 (A$_7$) |
| 51 | 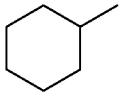 | F | p-CF$_3$/H | 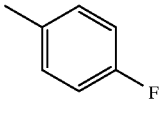 | 0,54 (A$_5$) |
| 52 | 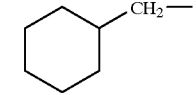 | F | p-CF$_3$/H | 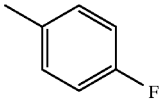 | 0,33 (A$_7$) |
| 53 | 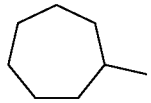 | F | p-CF$_3$/H | 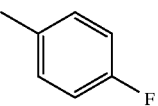 | 0,57 (A$_5$) |
| 54 |  | H | p-f/H | | 0,48 (A$_5$) |

TABLE 5-continued
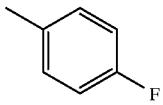
| Ex.-No. | E | R[18] | Z[1]/Z[2] | L | $R_f$ (eluent) |
|---|---|---|---|---|---|
| 55 | 4-F-C6H4-CH3 | F | p-CF3/H | iPr | 0,53 (A5) |
| 56 | 4-F-C6H4-CH3 | F | p-CF3O—/H | iPr | 0,26 (A4) |
| 57 | 4-F-C6H4-CH3 | F | p-Ph/H | iPr | 0,51 (A5) |
| 58 | 4-F-C6H4-CH3 | F | 3,5-(CF3)2 | iPr | 0,67 (A5) |
| 59 | 4-F-C6H4-CH3 | F | m-CF3O—/H | iPr | 0,26 (A4) |
| 60 | 4-F-C6H4-CH3 | H | m-Phe/H | iPr | 0,51 (A5) |
| 61 | 4-F-C6H4-CH3 | F | m-Phe/H | iPr | 0,62 (A5) |
| 62 | 4-F-C6H4-CH3 | OH | m-Phe/H | iPr | 0,27 (A5) |

TABLE 6

[Structure: pyridine with R19, Z-phenyl, CF3-phenyl, isopropyl, 4-F-phenyl, CH2OH substituents]

| Ex.-No. | Z | R19 | Rf (LM) |
|---|---|---|---|
| 63 | m-Cl | H | 0,68 (A5) |
| 64 | m-Cl | F | 0,62 (A5) |
| 65 | m-CH3 | F | 0,59 (A5) |

TABLE 7

[Structure: pyridine with R20, R21, L, 4-F-phenyl (×2), CH2OH substituents]

| Ex.-No. | R20 | R21 | L | Rf (eluent) |
|---|---|---|---|---|
| 66 | F | 2-Naphthyl | isopropyl | 0,59 (A5) |
| 67 | F | 1-Naphthyl | isopropyl | 0,57 (A5) |
| 68 | F | 2-Napthyl | cyclopentyl | 0,5 (A5) |
| 69 | F | 1-Naphthyl | cyclopentyl | 0.76 (A5) |
| 70 | F | 2-Naphthyl | cyclobutyl | 0,80 (A5) |
| 71 | OH | 2-Naphthyl | cyclohexyl | 0,52 (A5) |
| 72 | F | 1-Naphthyl | cycloheptyl | 0,55 (A5) |
| 73 | F | 2-Naphthyl | cycloheptyl | 0,60 (A5) |
| 74 | F | 5-CF3-Naphthyl-1 | cyclopentyl | 0,33 (A4) |
| 75 | H | 5-CF3-Naphthyl-1 | cyclopentyl | 0,2 (A4) |
| 76 | F | 5-CF3-Naphthyl-1 | isopropyl | 0,24 (A7) |
| 77 | OH | 6-CH3O-Naphthyl-2 | cyclopentyl | 0,29 (A5) |

TABLE 8

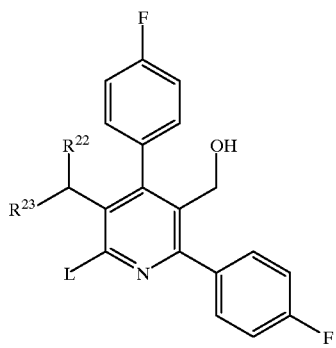

| Ex.-No. | R²² | R²³ | L | R_f (eluent) |
|---------|-----|-----|---|--------------|
| 78 | F | 4-methyl-8-trifluoromethylquinolin-3-yl | cyclopentylmethyl | 0,44 (A₅) |
| 79 | F | 6-methylpyridin-2-yl | isobutyl | 0,18 (A₅) |
| 80 | H | 6-methylpyridin-2-yl | isobutyl | 0,13 (A₅) |
| 81 | F | 3-methylquinolin-2-yl | isobutyl | 0,37 (A₅) |
| 82 | F | cyclopropyl | isobutyl | 0,62 (A₅) |

Example 83

2,4-di-(4-Fluorophenyl)-6-isopropyl-5-[2-(3-trifluoromethylphenyl)vinyl]-3-hydroxymethyl-pyridine

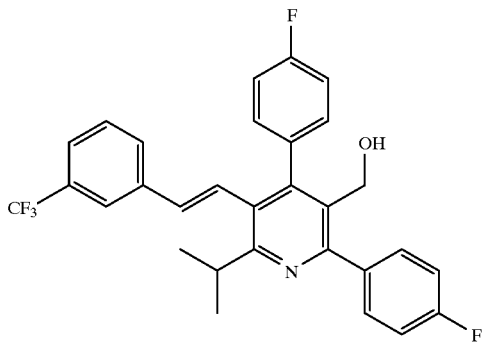

Under argon, 3.0 mml (3 mol; 6 eq.) of DIBAL-H are added to a solution of 269 mg (0.5 mmol) of the compound from Example XII in 10 g of dry toluene at −78° C. and the mixture is then stirred without a cooling bath for 4 h to +15° C. 40 ml of ethyl acetate and 20 ml of a 20% strength potassium sodium tartrate solution are added and the mixture is stirred for 10 min. The aqueous phase is separated off, and the organic layer is dried over Na₂SO₄, filtered and concentrated.

Yield: 250 mg (98% of theory)
R_f=0.38 (A₄)

Example 84

2,4-di-(4-Fluorophenyl)-6-isopropyl-5-[2-(3-trifluoromethylphenyl)ethyl]-3-hydroxy-methyl-pyridine

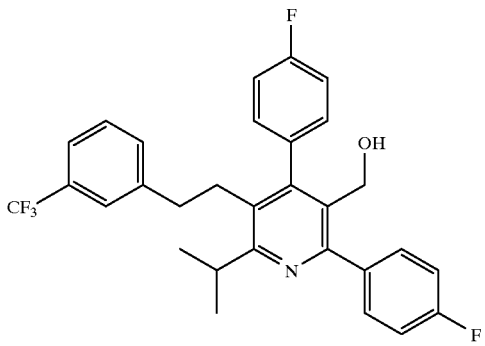

100 mg (0.196 mmol) of the compound from Example 83 are stirred at room temperature overnight in 20 g of methanol in the presence of 100 mg of Pd/C (10%) under a hydrogen atmosphere. The catalyst is then filtered off with suction through SiO₂ and washed with methanol, and the filtrate is concentrated. The residue is purified on 30 ml of silica gel by flash chromatography using toluene.

Yield: 71 mg (70.1% of theory)
R_f=0.25 (A₄)

Example 85

2,4-di-(4-Fluorophenyl)-6-isopropyl-5-[2-(3-trifluoromethyl-phenyl)-1,2-dihydroxyethyl]-3-hydroxymethyl-pyridine

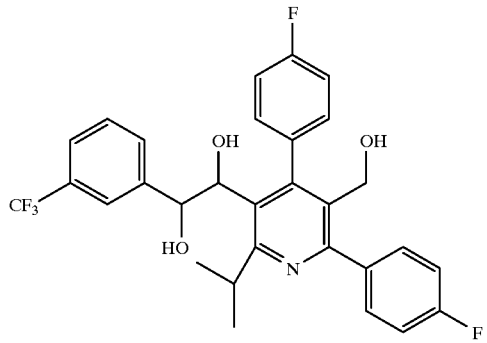

Analogously to Example 33, 76 mg (0.133 mmol) of the compound from Example XIII are reacted with 0.33 ml (0.333 mmol, 2.5 eq.) of DIBAL-H (1 molar in toluene).

Yield: 31 mg (43% of theory)

$R_f$=0.16 (toluene/ethyl acetate 8:2)

The compounds listed in Tables 9 and 10 are prepared according to these procedures:

TABLE 9

| Ex.-No. | T | $R_f$ (eluent) |
|---|---|---|
| 86 | 3-propyl-aniline | 0,24 ($A_5$) |
| 87 | 2-(trifluoromethyl)phenyl-propyl | 0,58 ($A_5$) |
| 88 | 2-(trifluoromethyl)phenyl-propenyl | 0,18 ($A_4$) |
| 89 | 2-propyl-aniline | 0,21 ($A_5$) |
| 90 | 4-pyridyl-propyl | 0,09 ($A_8$) |
| 91 | 4-fluorophenyl-butyl | 0,59 ($A_5$) |
| 92 | 4-(trifluoromethyl)phenyl-butyl | 0,55 ($A_5$) |
| 93 | 4-(trifluoromethyl)phenyl-propenyl | 0,56 ($A_5$) |
| 94 | 4-(trifluoromethyl)phenyl-sec-butyl | 0,45 ($A_9$) |

TABLE 9-continued
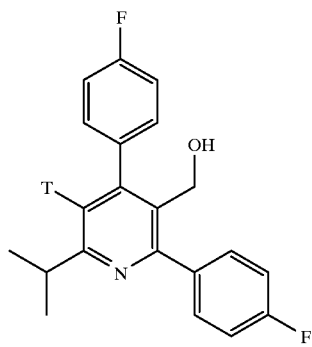
| Ex.-No. | T | $R_f$ (eluent) |
|---|---|---|
| 95 (E-Isomer) | 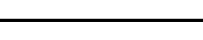 | 0,58 ($A_5$) |
| 96 (Z-Isomer) |  | 0,73 ($A_5$) |
| 97 | 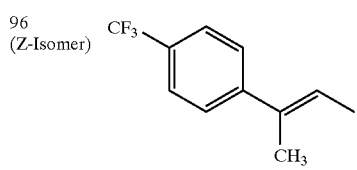 | 0,31 ($A_{10}$) |
| 98 | 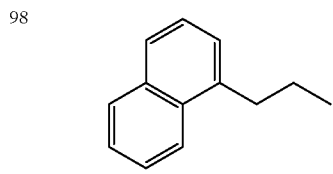 | 0,27 ($A_{10}$) |
| 99 |  | 0,33 ($A_4$) |
TABLE 9-continued
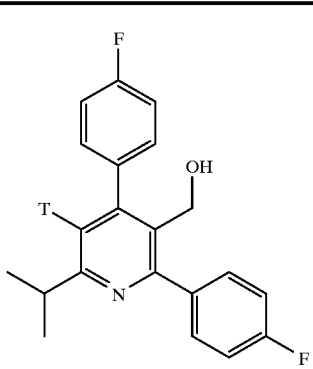
| Ex.-No. | T | $R_f$ (eluent) |
|---|---|---|
| 100 |  | 0,15 ($A_4$) |
| 101 | 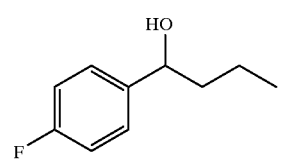 | 0,13 ($A_5$) |
| 102 | 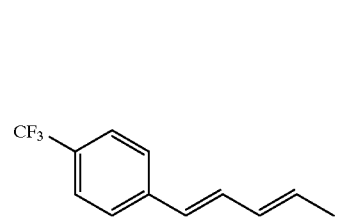 | 0,51 ($A_{11}$) |
| 103 | | 0,36 ($A_5$) |

TABLE 10

| Ex. No. | Structure | $R_f$ (eluent) |
| --- | --- | --- |
| 104 | 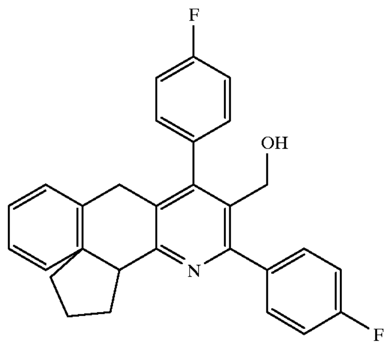 | 0.55 (Tol/EA = 9:1) |
| 105 | 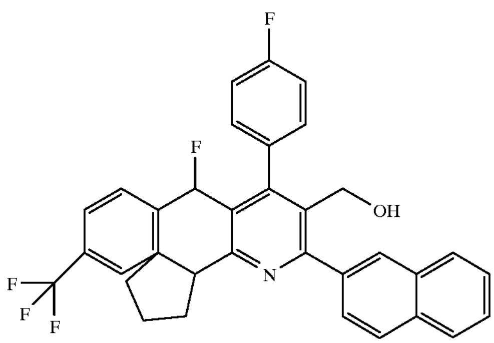 | 0.39 (PE/EA = 85:15) |
| 106 | 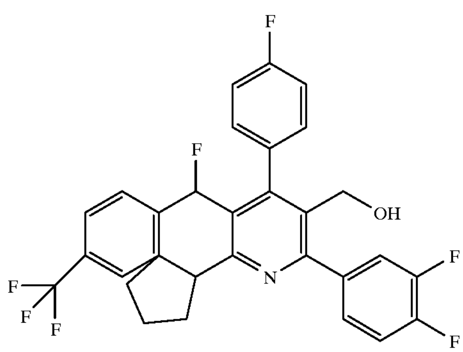 | 0.46 (PE/EA = 85:15) |
| 107 | 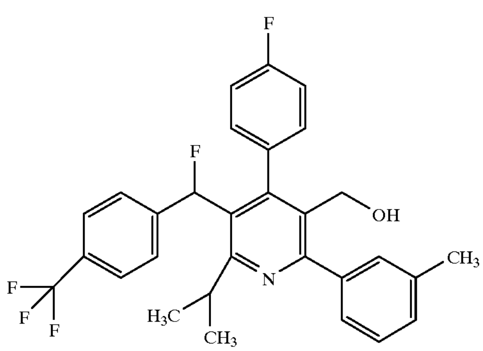 | 0.19 (PE/EA = 9:1) |

TABLE 10-continued

| Ex. No. | Structure | R$_f$ (eluent) |
|---|---|---|
| 108 | 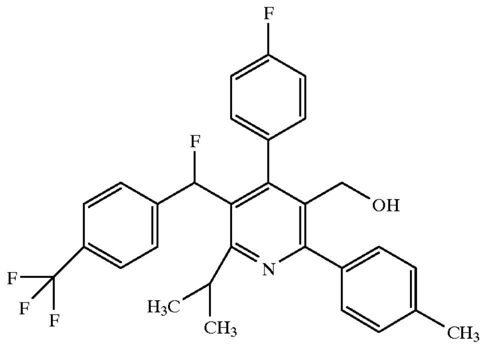 | 0.2 (PE/EA = 9:1) |
| 109 | 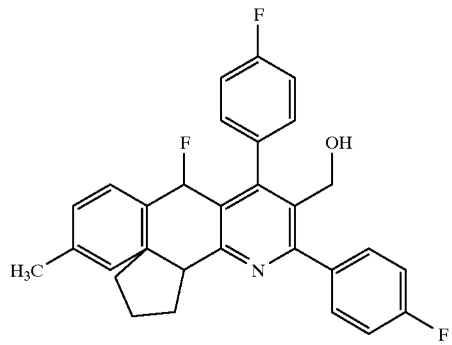 | 0.70 (Tol/EA = 9:1) |
| 110 | 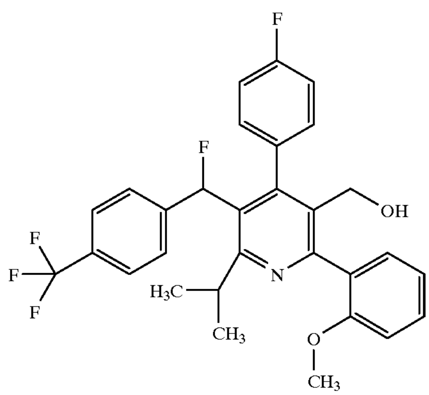 | 0.22 (PE/EA = 8:2) |
| 111 | 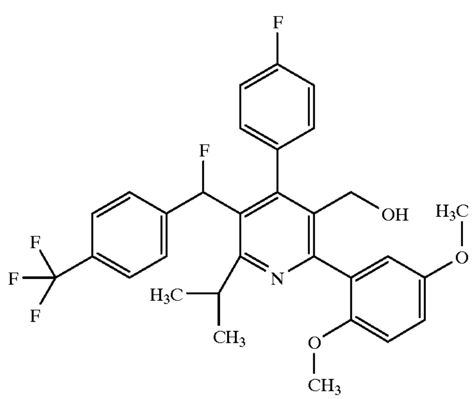 | 0.32 (PE/EA 8:2) |

TABLE 10-continued

| Ex. No. | Structure | R$_f$ (eluent) |
|---|---|---|
| 112 | 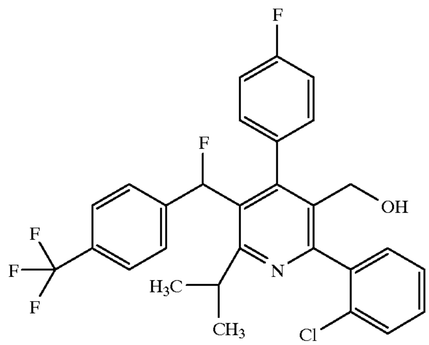 | 0.27 (PE:EA 8:2) |
| 113 | 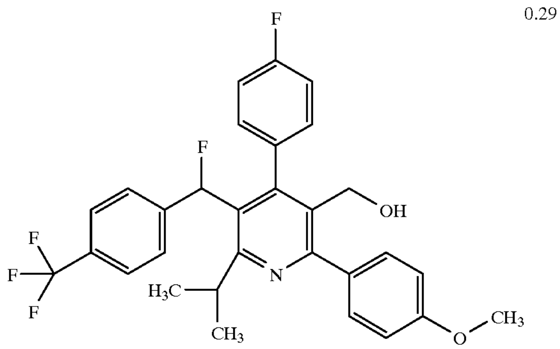 | 0.29 (PE/EA 8:2) |
| 114 | 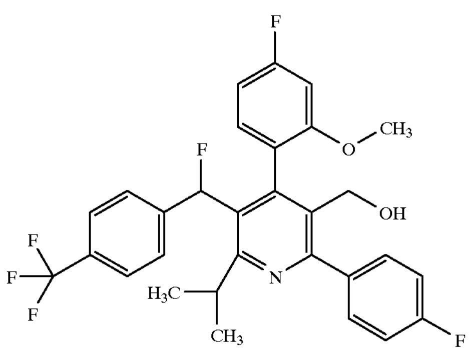 | 0.26 (PE/EA 8:2) |
| 115 | 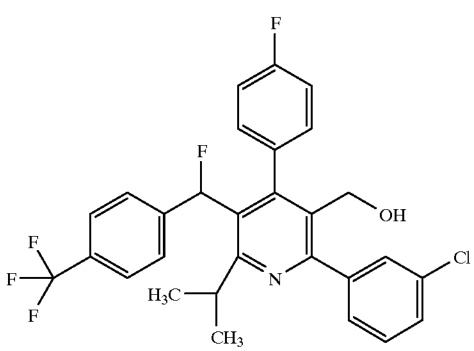 | 0.34 (PE/EA 84:15) |

TABLE 10-continued

| Ex. No. | Structure | $R_f$ (eluent) |
|---|---|---|
| 116 | 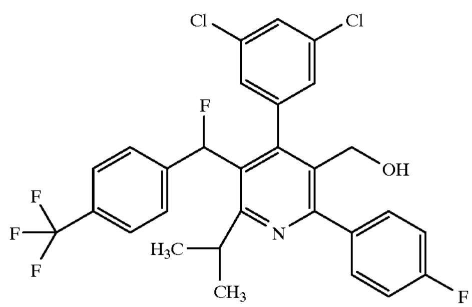 | 0.36 (PE/EA 9:1) |
| 117 | 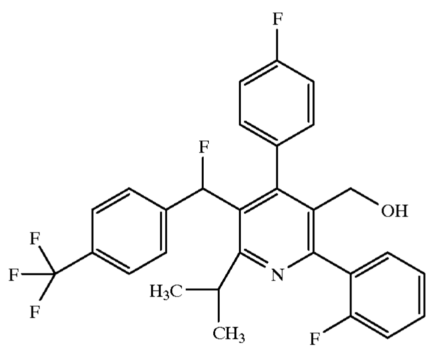 | 0.18 (PE/EA 85:15) |
| 118 | 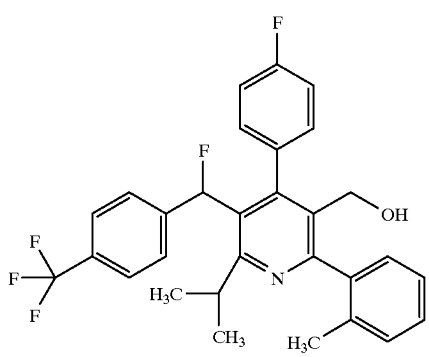 | 0.26 (PE/EA 84:15) |
| 119 | 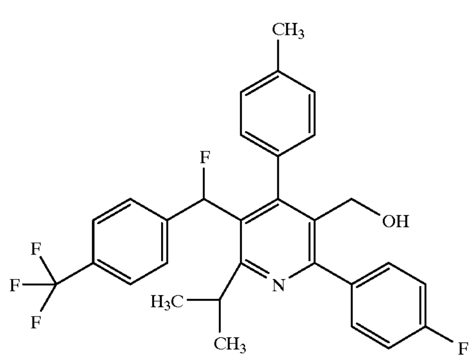 | 0.29 (PE/EA 84:15) |

TABLE 10-continued

| Ex. No. | Structure | $R_f$ (eluent) |
|---|---|---|
| 120 | 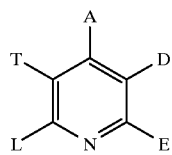 | 0.07 (PE/EA 9:1) |

We claim:

1. A 2-Aryl-substituted pyridine of the formula (I)

(I)

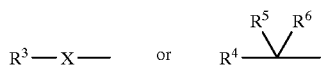

in which

A and E are identical or different and represent aryl having 6 to 10 carbon atoms, which is optionally substituted up to 3 times identically or differently by halogen, hydroxyl, trifluoromethyl, trifluoromethoxy or by straight-chain or branched alkyl, acyl, hydroxyalkyl or alkoxy each having up to 7 carbon atoms, or by a group of the formula —$NR^1R^2$, in which $R^1$ and $R^2$ are identical or different and denote hydrogen, phenyl or straight-chain or branched alkyl having up to 6 carbon atoms, D represents straight-chain or branched alkyl having up to 8 carbon atoms, which is substituted by hydroxyl, L represents cycloalkyl having 3 to 8 carbon atoms or straight-chain or branched alkyl having up to 8 carbon atoms, which is optionally substituted by cycloalkyl having 3 to 8 carbon atoms or by hydroxyl, T represents a radical of the formula $R^3$—X— or $R^4\underset{}{\overset{R^5\ R^6}{\diagup}}$ in which $R^3$ and $R^4$ are identical or different and denote cycloalkyl having 3 to 8 carbon atoms, or
denote aryl having 6 to 10 carbon atoms, which is optionally substituted up to 3 times identically or differently by trifluoromethyl, trifluoromethoxy, halogen, hydroxyl, carboxyl, nitro, by straight-chain or branched alkyl, acyl, alkoxy or alkoxycarbonyl each having up to 6 carbon atoms or by phenyl, phenoxy or phenylthio, which for their part can be substituted by halogen, trifluoromethyl or trifluoromethoxy,
and/or the aryl is optionally substituted by a group of the formula —$NR^7R^8$, in which $R^7$ and $R^8$ are identical or different and have the meaning of $R^1$ and $R^2$ indicated above, X denotes straight-chain or branched alkylene or alkenylene each having up to 10 carbon atoms, each of which is optionally substituted up to 2 times by hydroxyl or halogen, $R^5$ denotes hydrogen and $R^6$ denotes hydrogen, mercapto, halogen, azido, trifluoromethyl, hydroxyl, trifluoromethoxy, straight-chain or branched alkoxy having up to 5 carbon atoms or a radical of the formula —$NR^9R^{10}$, in which $R^9$ and $R^{10}$ are identical or different and have the meaning of $R^1$ and $R^2$ indicated above, or $R^5$ and $R^6$ together with the carbon atom form a carbonyl group, or a salt thereof.

2. A 2-Aryl-substituted pyridine of the formula according to claim 1, in which

A and E are identical or different and represent phenyl or naphthyl, each of which is optionally substituted up to 2 times identically or differently by fluorine, chlorine, bromine, hydroxyl, trifluoromethyl, trifluoromethoxy, nitro or by straight-chain or branched alkyl, acyl or alkoxy each having up to 6 carbon atoms or by a group of the formula —$NR^1R^2$, in which $R^1$ and $R^2$ are identical or different and denote hydrogen, phenyl or straight-chain or branched alkyl having up to 4 carbon atoms, D represents straight-chain or branched alkyl having up to 7 carbon atoms, which is substituted by hydroxyl, L represents cyclopropyl, cyclobutyl, cyclopentyl, cyclohexyl or cycloheptyl, or
represents straight-chain or branched alkyl having up to 6 carbon atoms, which is optionally substituted by cyclopropyl, cyclobutyl, cyclopentyl, cyclohexyl, cycloheptyl or by hydroxyl, T represents a radical of the formula

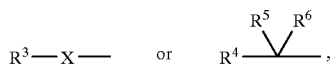

in which

R$^3$ and R$^4$ are identical or different and denote cyclopropyl, cyclopentyl or cyclohexyl, or denote naphthyl, or phenyl, which are optionally substituted up to 3 times identically or differently by trifluoromethyl, trifluoromethyoxy, fluorine, chlorine, bromine, hydroxyl, carboxyl, by straight-chain or branched alkyl, acyl, alkoxy or alkoxycarbonyl each having up to 5 carbon atoms or by phenyl, phenoxy or phenylthio, which for their part can be substituted by fluorine, chlorine, bromine, trifluoromethyl or trifluoromethoxy, and/or when R$^3$ and R$^4$ are phenyl or naphthyl, then these are optionally substituted by a group of the formula —NR$^7$R$^8$, in which R$^7$ and R$^8$ are identical or different and have the meaning of R$^1$ and R$^8$ indicated above, X is straight-chain or branched alkylene or alkenylene each having up to 8 carbon atoms, each of which is optionally substituted up to 2 times by hydroxyl or fluorine, R$^5$ denotes hydrogen and R$^6$ denotes hydrogen, fluorine, chlorine, bromine, azido, trifluoromethyl, hydroxyl, mercapto, trifluoromethoxy, straight-chain or branched alkoxy having up to 4 carbon atoms or a radical of the formula —NR$^9$R$^{10}$, in which R$^9$ and R$^{10}$ are identical or different and have the meaning of R$^1$ and R$^2$ indicated above, or R$^5$ and R$^6$ together with the carbon atom form a carbonyl group, or a salt thereof.

3. A 2-Aryl-substituted pyridine of the formula according to claim 1, in which

A and E are identical or different and represent phenyl or naphthyl, each of which is optionally substituted up to 2 times identically or differently by fluorine, chlorine, bromine, hydroxyl, trifluoromethyl, trifluoromethoxy, nitro or by straight-chain or branched alkyl or alkoxy each having up to 5 carbon atoms, D represents straight-chain or branched alkyl having up to 6 carbon atoms, which is substituted by hydroxyl, L represents cyclopropyl, cyclobutyl, cyclopentyl, cyclohexyl or cycloheptyl, or represents straight-chain or branched alkyl having up to 5 carbon atoms, which is optionally substituted by cyclopentyl or cyclohexyl, T represents a radical of the formula

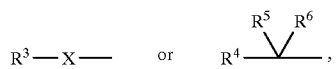

in which

R$^3$ and R$^4$ are identical or different and denote cyclopropyl, or denote phenyl, which is optionally substituted up to 2 times identically or differently by trifluoromethyl, trifluoromethyoxy, fluorine, chlorine, bromine, hydroxyl, carboxyl, anino by straight-chain or branched alkyl, alkoxy or alkoxycarbonyl each having up to 4 carbon atoms or by phenyl, phenoxy or phenylthio, which for their part can be substituted by fluorine, chlorine, bromine, trifluoromethyl or trifluoromethoxy, X denotes straight-chain or branched alkylene or alkenylene each having up to 6 carbon atoms, each of which is optionally substituted up to 2 times by hydroxyl or fluorine, R$^5$ denotes hydrogen and R$^6$ denotes hydrogen, fluorine, chlorine, bromine, azido, amino, trifluoromethyl, hydroxyl, trifluoromethoxy, methoxy or mercapto, or R$^5$ and R$^6$ together with the carbon atom form a carbonyl group, or a salt thereof.

4. A 2-Aryl-substituted pyridine of the formula according to claim 1, in which

A represents phenyl, which is optionally substituted up to 2 times identically or differently by fluorine, chlorine, methyl, nitro or methoxy.

5. Pharmaceutical composition which comprises an anti-arteriosclerotic effective amount of a 2-substituted pyridine according to claim 1 and a pharmacologically acceptable formulation auxiliary.

6. A method of treating arteriosclerosis in a patient in need thereof which comprises administering to such a patient an amount effective therefor of a compound or salt thereof according to claim 1.

* * * * *